(12) United States Patent
Arnitz et al.

(10) Patent No.: US 10,486,838 B2
(45) Date of Patent: Nov. 26, 2019

(54) TRANSPORT AND TRANSFER CONTAINER FOR A LIQUID MEDIUM

(71) Applicant: Roche Diagnostics Operations, Inc., Indianapolis, IN (US)

(72) Inventors: Theo Arnitz, Waghaeusel (DE); Stefan Hartig, Achern (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 893 days.

(21) Appl. No.: 14/105,186

(22) Filed: Dec. 13, 2013

(65) Prior Publication Data
US 2014/0102048 A1 Apr. 17, 2014

Related U.S. Application Data

(63) Continuation of application No. PCT/EP2012/061079, filed on Jun. 12, 2012.

(30) Foreign Application Priority Data

Jun. 16, 2011 (EP) ..................................... 11170210

(51) Int. Cl.
| | |
|---|---|
| *B65B 3/04* | (2006.01) |
| *A61M 5/00* | (2006.01) |
| *A61M 5/28* | (2006.01) |
| *A61J 1/06* | (2006.01) |
| *A61J 1/20* | (2006.01) |

(52) U.S. Cl.
CPC .................. *B65B 3/04* (2013.01); *A61J 1/062* (2013.01); *A61J 1/2089* (2013.01); *A61M 5/008* (2013.01); *A61M 5/283* (2013.01); *A61J 1/201* (2015.05); *A61J 1/2013* (2015.05)

(58) Field of Classification Search
CPC .. B65B 3/04; A61J 1/062; A61J 1/2089; A61J 1/201; A61J 1/2013; A61M 5/283; A61M 5/008
See application file for complete search history.

(56) References Cited

U.S. PATENT DOCUMENTS

| | | | |
|---|---|---|---|
| 4,201,207 A | 5/1980 | Buckles et al. | |
| 4,765,512 A | 8/1988 | Bull | |
| (Continued) | | | |

FOREIGN PATENT DOCUMENTS

| | | |
|---|---|---|
| EP | 2258426 A1 | 12/2010 |
| WO | 2008/083209 A2 | 7/2008 |
| WO | 2009/119496 A1 | 10/2009 |

*Primary Examiner* — Amber R Stiles

(57) ABSTRACT

A production method for producing a transport and transfer receptacle for at least one fluid medium, for example, for at least one sterile liquid is proposed. The method comprises supplying at least one container for receiving the fluid medium. At least one energy unit is supplied. The energy unit effects—for example, complete—emptying of the fluid medium from the container when the transport and transfer receptacle is used. The fluid medium is introduced into the container and the container is closed. The fluid medium is charged with positive pressure, for example, using the energy unit. The positive pressure is maintained until the fluid medium is removed. Furthermore, a transport and transfer receptacle which can be produced according to the production method and which has at least one packaging is proposed.

15 Claims, 4 Drawing Sheets

(56) References Cited

U.S. PATENT DOCUMENTS

| | | | |
|---|---|---|---|
| 5,858,001 A * | 1/1999 | Tsals | A61M 5/14248 604/135 |
| 7,214,221 B2 | 5/2007 | Fentress et al. | |
| 7,252,651 B2 | 8/2007 | Haider et al. | |
| 7,470,258 B2 | 12/2008 | Barker et al. | |
| 7,670,314 B2 | 3/2010 | Wall et al. | |
| 2004/0133159 A1 | 7/2004 | Haider et al. | |
| 2007/0293826 A1 * | 12/2007 | Wall | A61M 5/19 604/200 |
| 2010/0262077 A1 | 10/2010 | Beebe et al. | |
| 2011/0015609 A1 | 1/2011 | Matsumoto | |
| 2014/0102048 A1 * | 4/2014 | Arnitz | A61M 5/008 53/467 |

* cited by examiner

TRANSPORT AND TRANSFER CONTAINER FOR A LIQUID MEDIUM

CROSS-REFERENCE TO RELATED APPLICATIONS

This application is a continuation of PCT/EP2012/061079, filed Jun. 12, 2012, which is based on and claims priority to EP 11170210.6, filed Jun. 16, 2011, which is hereby incorporated by reference.

BACKGROUND

The present disclosure generally relates to a method for producing a transport and transfer receptacle for at least one fluid medium, a supply method for supplying at least one fluid medium and to a transport and transfer receptacle for at least one fluid medium and, in particular, to a method for producing a transport and transfer receptacle for at least one fluid medium, a supply method for supplying at least one fluid medium and to a transport and transfer receptacle for at least one fluid medium for medical technology in order to be able to store fluid media, in particular liquids, under sterile conditions for a number of weeks or months and subsequently to be able to supply the media in a simple and reliable manner, for example to an infusion means, an injection device or a medication device, for example an insulin pump or another type of medication pump.

The prior art discloses a multiplicity of receptacles for fluid media, in particular liquids, which receptacles can be used, in principle, for storing, transporting and transferring fluid media and optionally for an injection of fluid media of this type.

For example, one injection device discloses a device suitable, for example, for self medication. The injection device comprises a housing, as a base for placing onto a skin surface of a patient. The base accommodates an injection needle which can simultaneously penetrate a skin surface of a patient and a septum of a liquid reservoir. Furthermore, a manually operable compression spring which exerts pressure on an injectable liquid composition within the reservoir is provided. An overall disadvantage of this system however is that the charging of the receptacle with positive pressure, which charging is carried out by a patient or trained medical staff directly during the injection, is always coupled to the injection itself. For this purpose, the patient or the trained medical staff has himself to apply the energy required for the pressurization and for the perforation. A further problem arises due to the fact that the liquid generally contains gas bubbles which may possibly pass into the body tissue of the patient during simultaneous pressurization and injection.

Another injection device for use on a skin surface of a patient comprises a base which can be adhesively bonded onto the skin surface. Furthermore, a cartridge containing a medicament is provided. When placed onto the skin, a rise in pressure in the cartridge and a production of a fluid connection to an injection needle are produced simultaneously by a corresponding mechanism. However, a disadvantage of this construction is again that gas bubbles may form in the cartridge, which gas bubbles cannot be dissolved because of the rise in pressure and the penetration of the skin surface by the injection needle being produced simultaneously, and therefore the gas bubbles can enter the body tissue. A further disadvantage resides in the complexity of the described system, since the simultaneousness of the operations described necessitates interaction of a plurality of components, in particular interaction of a plurality of component parts. Furthermore, a disadvantage of the described construction can consist in that movement of a pressurization system parallel to a skin surface takes place in a state in which an injection needle has already penetrated the skin surface, and this may result in an increased pain load. A further disadvantage consists in that a tightness check of the system and of the individual system components is not possible until during use. If, however, it should turn out during use that, due to defective interaction of individual system components, there is a leak, liquid may escape during the injection operation without the injection operation still being able to be broken off in a controlled manner or repeated with a defined injection quantity.

Further injection systems in which mechanical pressurization can take place during an injection operation are known. However, these systems also have the above-described disadvantages, in particular the disadvantages of gas bubble formation and the disadvantage that a tightness check generally does not take place until during use of the described systems. Furthermore, some of the described systems are extremely complex technically. Further disadvantages consist in that the fluid receptacles can generally only be changed with difficulty or with admission of air.

Numerous different exemplary embodiments of another medication device for applying a pressurized medicament liquid describes, for example, the use of a liquid reservoir in the form of a bag which is accommodated in a housing. The housing comprises a puncturing element which can puncture a bag wall of the reservoir. Before application of the medicament, the liquid reservoir is placed under pressure, and the wall of the reservoir is punctured. This puncturing can take place in different ways, for example automatically or by appropriate pressing onto a skin surface. Furthermore, various exemplary embodiments disclose a sterile external packaging, different pressurization times, different types of pressurization mechanism, pressurization when screwing a cap on, and various safety mechanisms.

Therefore, there is a need for a transport and transfer receptacle for a fluid medium and a corresponding production method which at least substantially avoid the disadvantages of known transport and transfer receptacles and production methods such as to be designed in a simple manner, is intended also to be usable for large quantities of liquid and is intended to completely remove air bubbles arising during the filling.

SUMMARY

According to the present disclosure, a production and supply method for producing a transport and transfer receptacle for at least one fluid medium is presented. At least one container for receiving the fluid medium is supplied. At least one energy unit is supplied. The energy unit effects the emptying of the fluid medium from the container when the transport and transfer receptacle is used. The fluid medium is introduced into the container and closing the container is closed. The fluid medium is charged with positive pressure using the energy unit. The positive pressure is maintained until the fluid medium is removed. At least the container is packed in the state charged with positive pressure in at least one packaging.

Accordingly, it is a feature of the embodiments of the present disclosure to provide for a transport and transfer receptacle for a fluid medium and a corresponding production method which at least substantially avoid the disadvantages of known transport and transfer receptacles and production methods such as to be designed in a simple manner, is intended also to be usable for large quantities of liquid and is intended to completely remove air bubbles arising during the filling. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
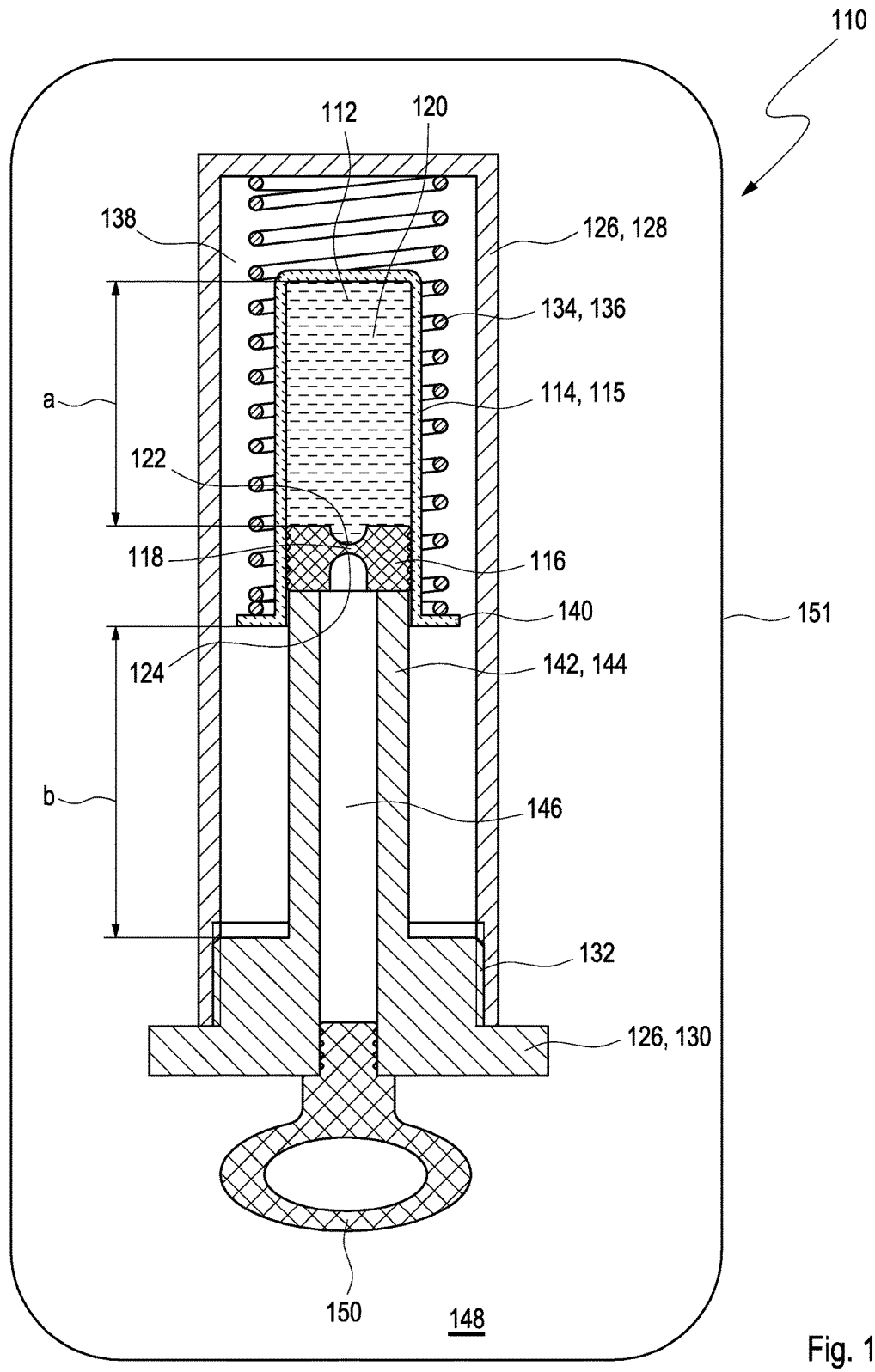
FIG. 1 illustrates a transport and transfer receptacle according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

Within the scope of the present invention, the terms "comprises", "contains" and "has" and corresponding grammatical modifications thereof are understood as meaning that the terms can include both the possibility of a definitive listing of components in the sense of "consists of" and the possibility of a non-definitive listing. For example, the expressions "A has B", "A contains B" and "A comprises B" can thus be understood in such a manner that A either exclusively consists of B or that A contains at least one further component in addition to B.

A production method for producing a transport and transfer receptacle for at least one fluid medium is proposed. A transport and transfer receptacle here should generally be understood as meaning a receptacle by which a fluid medium, for example, a liquid, for example, a liquid therapeutic agent and/or diagnostic agent, can be transported and supplied. Transport and/or supply can take place for example under sterile conditions. The transport can take place, for example, from a manufacturer to a wholesaler, from a wholesaler to a retailer or from a retailer to a final customer or user and can optionally also include, for example, storage. A transfer should be understood as meaning an operation in which the fluid medium can be conveyed out of the transport and transfer receptacle into a further device, for example a further container and/or a fluid device, or can be conveyed out of the transport and transfer receptacle in another manner such that the transport and transfer receptacle can be completely or partially emptied.

As explained above, the fluid medium can, for example, comprise at least one liquid. For example, the liquid can be at least one sterile liquid, i.e. a liquid which can be produced and/or decanted and/or stored and/or used under sanitized conditions.

The method can comprise the following steps which can preferably, but not necessarily, be carried out in the sequence presented below. Furthermore, individual method steps or a plurality of the method steps mentioned can also be carried out repeatedly, in parallel in time or overlapping in time. Furthermore, additional method steps which are not mentioned below can be provided. At least one container for receiving the fluid medium can be supplied. At least one energy unit can be supplied, such as, for example, an integrated energy unit. The energy unit can effect a—for example, complete—emptying of the fluid medium from the container when the transport and transfer receptacle is used. The fluid medium can be introduced into the container and the container can be closed. The fluid medium can be charged with a positive pressure, for example, using the energy unit. The positive pressure can be maintained until the fluid medium is removed.

The transport and transfer receptacle can therefore comprise at least one container for receiving the fluid medium. A container here can generally be understood as meaning a device which can comprise at least one interior for receiving the fluid medium and at least one container wall which can retain the fluid medium in the interior. The container can be produced, for example, entirely or partially, from a material selected from the group comprising of glass and/or plastic.

An energy unit can be understood as meaning a device which can affect the complete, or partial, emptying of the fluid medium from the container. For this purpose, the energy unit can, for example, exert a pressure on the fluid medium mechanically. The energy unit can comprise for this purpose, for example, one or more devices which can reduce a volume of the interior of the container such as, for example, a piston which can move in the interior and/or a stopper. Furthermore, the energy unit can comprise at least one energy accumulator which can accumulate a quantity of energy, preferably a mechanical quantity of energy such as, for example, at least one spring accumulator. The energy accumulator can be coupled, for example, to the device which can exert pressure on the fluid medium. The energy device can comprise, for example, at least one mechanical spring element which can be coupled to at least one piston and/or stopper of the energy unit. The spring element can be, for example, at least one helical compression spring, a sprung spring and/or spiral spring. The mechanical quantity of energy stored in the energy unit can be configured so that the quantity of energy can be sufficient for—as in one embodiment, complete—emptying of the fluid medium from the container, preferably also for a shelf time of at least two weeks, at least four weeks, at least two months or even at least four months and, in particular, even at least one year or a number of years or for at least the "shelf lifetime" of the product.

Use of the transport and transfer receptacle can be understood as meaning an operation in which the fluid medium can be transferred out of the container of the transport and transfer receptacle as intended. The terms including the use, the intended use, complete or partial emptying and transfer of the fluid medium out of the container can be used substantially synonymously. The transfer can take place, for example, using the energy unit, for example by the mechanical energy accumulator of the energy unit being discharged, the energy unit exerting a pressure on the fluid medium, and the fluid medium being transferred out of the container, for example, after a fluid connection has been produced.

Introducing the fluid medium into the container can generally be understood as meaning a decanting of the fluid medium, in which the container can be completely, or partially, filled with the at least one fluid medium. The introducing can take place, for example, in an automated manner, for example, by a corresponding decanting system.

Closing of the container can be understood as meaning an operation in which the container is closed. This can take place, for example, by at least one closure element such as, for example, by at least one stopper such as, for example, a perforable stopper and, in one embodiment, by least one perforable, displaceably mounted stopper. The closure element can even be part of the container. The closing can take place in such a manner that the fluid medium can be retained in an interior of the container and can no longer leave the interior, at least without subsequent production of a fluid connection to the interior.

Charging the fluid medium with positive pressure can be understood as meaning an operation, after the carrying out of which the fluid medium in the container can have a pressure which can lie above the ambient pressure, i.e. above a normal pressure, for example, a pressure of at least 1.2 bar in one embodiment, at least 1.5 bar in another embodiment, and at least 2 bar in another embodiment. The pressurization can be undertaken by a manufacturer of the transport and transfer receptacle, i.e., for example, within the scope of a production method in an installation or in a factory in which method steps can be carried out.

Maintaining the positive pressure until the fluid medium can be removed can be understood as meaning an operation in which the fluid medium in the container of the transport and transfer receptacle can have a pressure above an ambient pressure, a pressure of at least 1.2 bar in one embodiment, of at least 1.5 bar in another embodiment and, in another embodiment, of at least 2 bar, until an intended transfer of the fluid medium out of the container. For example, the fluid medium in the container can initially be charged during production with an initial pressure above the ambient pressure, with the positive pressure being maintained in such a manner, until the fluid medium can be removed, that the positive pressure does not drop to less than about 50% of the initial pressure in one embodiment, to not less than about 70% in another embodiment, to not less than about 80% in another embodiment, and, in another embodiment, to not less than about 90% of the initial pressure, until the fluid medium can be removed. This can take place, for example, by a corresponding design of the energy unit, for example by a corresponding mechanical energy accumulator being selected, which energy accumulator can remain for at least two weeks, for at least four weeks, at least one month, at least two months, at least four months, at least a year or a number of years or for at least the entire shelf lifetime of the product, in a tensioned state such that the above-described pressure conditions can be satisfied. Furthermore, a correspondingly tight container can also be used.

The production method can be carried out in such a manner that the production method can further comprise packing at least the container of the transport and transfer receptacle in the state charged with positive pressure in at least one packaging.

The packing step can be carried out after the charging of the fluid medium with positive pressure has been carried out. Packing can be understood as meaning a process in which at least part of the transport and transfer receptacle which can comprise at least the container can be completely, or at least partially, covered by the at least one packaging. In addition to the container, one or more further elements of the transport and transfer receptacle can be completely, or partially, covered by the packaging. For example, at least the container and the energy unit can be entirely, or partially, packed, in a state in which the fluid medium can be charged with positive pressure by the energy unit. For example, the container and the energy unit can form a unit which can be accommodated in the packaging. The packaging can protect the transport and transfer receptacle from environmental influences, such as, for example, air, moisture, mechanical influences or combinations of the environmental influences mentioned and/or other environmental influences. For example, the packaging can comprise a sterile packaging, i.e. a germproof packaging, and/or a packaging which can be impermeable to air. For example, the packaging can comprise at least one plastic packaging. The container, and optionally one or more further parts, of the transport and transfer receptacle can thus be sealed into a plastic packaging, for example, a film packaging, for example into a "blister pack".

Furthermore, the packaging can contain at least one identification marking, for example an identification marking of the transport and transfer receptacle and/or an identification marking of the fluid medium as an integral or separate part. For example, a product-compliant identification marking can be contained. This identification marking can comprise, for example, at least one information item which can identify the fluid medium and/or the properties thereof and/or the use thereof. The identification marking can comprise, for example, at least one information item which can be readable by a person and/or at least one information item which can be readable by a machine. The at least one information item can be selected, for example, from the group consisting of: identity of the fluid medium, in particular type and/or concentration of at least one active compound in the fluid medium; manufacturer details; batch number of the fluid medium, use of the fluid medium; production date of the fluid medium; expiry date and/or use by date of the fluid medium. The identification marking can be applied, for example, on the packaging and/or introduced into the packaging. For example, the identification marking can comprise at least one imprint on the packaging and/or at least one identification label which can be adhesively bonded onto the packaging. Other types of identification marking can also be possible.

The production method can furthermore be carried out in particular in such a manner that, after the charging of the fluid medium with positive pressure has been carried out and before the transport and transfer receptacle can be used, the transport and transfer receptacle can be stored for a time period of at least two to three weeks, in a state charged with positive pressure and packed. The storage can therefore in particular also take place after the packing has been carried out, i.e. in the packed state of the transport and transfer receptacle.

Use here can generally be understood as meaning an operation in which the fluid medium can be supplied from the interior of the container of the transport and transfer receptacle, for example, by a fluid connection being produced between the interior and an exterior and/or a vessel, through which the fluid medium can be transferred out of the container. The storage can take place, for example, directly at the manufacturer or else at a wholesaler or retailer before the transport and transfer receptacle is transported to a user, for example to a doctor, care staff or to a patient. Accordingly, the fluid medium can be charged with positive pressure in particular by the manufacturer, i.e. not by a user using the transport and transfer receptacle as intended.

Storage can generally be understood as meaning an operation in which the transport and transfer receptacle is not used and is preferably stationary. The storage can take place, for example, at the manufacturer and/or also at a distributor and/or at a retailer and/or at a wholesaler. The storage can take place under controlled conditions in which, for example, an ambient temperature is adjusted to a predetermined range.

In the introduction of the fluid medium, first at least one gas bubble can furthermore be produced in the container. The charging of the fluid medium with positive pressure can then be carried out in such a manner that the gas bubble can completely disappear after a waiting period, for example a waiting period of at least one hour or of at least two hours, for example after a waiting period of one hour to a week or after a waiting period of two hours to a week, thus resulting in a transport and transfer receptacle which can be free from gas bubbles. For example, the charging of the fluid medium with positive pressure can be carried out in such a manner that the magnitude of the positive pressure with which the fluid medium can be charged can be selected in such a manner that the gas bubble can completely dissolve at least after the waiting period mentioned, which can be spent in particular at the manufacturer. This can take place, for example, by corresponding dimensioning of the mechanical energy accumulator of the energy unit such that, for example, the pressurization with a corresponding positive pressure can take place.

As explained above, method steps and also the optional packing step can be carried out before the transport and transfer receptacle is sold to a customer, in particular to a final customer. A customer here can generally be understood as meaning a person using the transport and transfer receptacle as intended. The customer can be a doctor or a hospital, a nursing facility, a care facility for old people or else a patient himself.

In the charging of the fluid medium with positive pressure, at least one spring element of the transport and transfer receptacle, such as, at least one spring element of the energy unit, for example at least one energy accumulator of the energy unit, can be tensioned. Tensioning here can be understood as meaning an at least partially reversible accumulation of mechanical energy in the spring element, for example by the spring element being stretched or compressed.

The spring element can act on at least one displaceable section of the container, for example on at least one stopper such as, for example, on at least one perforable stopper, for example on a stopper which can move in the container in such a manner that it can influence the volume of an interior of the container. For example, the container can comprise at least one tubular container wall, for example a tubular container which can be entirely, or partially, produced from glass and/or plastic and in which the at least one stopper can be introduced, for example in such a manner that the stopper can move parallel to an axis of the tubular container.

The stopper can be understood as meaning a sealing element which can close the container, for example reversibly. The stopper can be, for example, in the shape of a cylinder or can be of substantially cylindrical design, for example with a round, oval or polygonal cross section in a section direction perpendicularly to an axis of the container, for example an axis of rotation of the container. An outside diameter of the stopper can be matched, for example, to an inside diameter of an interior of the container, for example to a diameter or equivalent diameter of a tubular container. The stopper can preferably be mounted so as to be entirely, or partially, moved in the container. A perforable stopper can be understood in general as meaning a stopper which can be perforated by at least one needle element, for example by a cannula, a hollow needle or a solid needle, by application of customary forces in such a manner that a fluid connection to the interior of the container can be produced through the stopper. For example, the stopper can be designed in such a manner that it can be perforated manually. For this purpose, the stopper can be produced, for example, from a plastics material such as, for example, an elastomer material such as, for example, a rubber material. The stopper can have, for example, at least one perforable region which in one embodiment can have a thickness of not more than about 5 mm, in another embodiment, a thickness of not more than about 3 mm and, in another embodiment, a thickness of not more than about 2 mm, which thickness can be bored through upon perforation by the needle element.

The charging of the fluid medium with positive pressure can be carried out in such a manner that the positive pressure can assume at least a pressure level required for transferring the fluid medium out of the container. For example, this can take place by the transport and transfer receptacle being configured for a certain type of transfer, for example by a corresponding perforation device. For example, a corresponding transfer cross section and a corresponding transfer length can be produced here, wherein, after the charging of the fluid medium with positive pressure has been carried out, the pressure level can be set in such a manner that, for example taking into consideration corresponding flow properties, the pressure can be sufficient for a transfer of the fluid medium by the transfer route. This pressure can be determined, for example, analytically, empirically or semi-empirically, for example taking into consideration the Hagen-Poiseuille law.

The container can be designed in such a manner that, after the charging of the fluid medium with positive pressure has been carried out and before removal of the fluid medium, i.e. before an intended transfer of the fluid medium out of the interior of the container, the fluid medium can be in contact exclusively with a wall of the container and with a perforable section of the container such as, for example, a perforable stopper. For example, the container can be of tubular design and can comprise a container wall and the perforable stopper, and therefore the fluid medium can be in contact exclusively with these elements. This can have advantages with regard to product stability and/or fluid stability over a prolonged storage time. For example, the tubular container can be closed at one end and circumferentially by the container wall, for example a container wall made from glass material and/or plastic material, and, furthermore, by one stopper such as, for example, one perforable stopper such as, for example, a perforable stopper which can be mounted displaceably in the tubular container. For example, the perforable stopper, firstly, can therefore be part of the energy unit and can charge the fluid medium with the positive pressure and, secondly, can perforate, i.e. for producing a fluid connection between an exterior and the interior of the container.

After the charging of the fluid medium with positive pressure has been carried out, for example between carrying out the charging of the fluid medium with positive pressure and an intended removal of the fluid medium, the container can be without a fluid connection between an interior of the container, the interior receiving the fluid medium, and a surroundings of the container. The container can thus be designed, for example, without valves, closeable inlets and/ or outlets or similar fluid connections. The container can thus be designed in such a manner that a fluid connection can be produced, at least without destroying the container or parts thereof, exclusively by perforating at least one perforable section of the container, for example perforating a perforable stopper. For example, the container can have at least one perforable section through which the fluid medium can be removed after perforating the perforable section, for example at least one perforable stopper.

The container, and preferably the entire transport and transfer receptacle, can in particular be designed to be free from electric components. The above-described energy unit can thus be designed, for example, entirely, or partially, as a mechanical energy unit, for example as a moveable stopper, which can be connected to a mechanical energy accumulator, for example at least one spring element, such that the fluid medium can be charged with positive pressure via the at least one moveable stopper via precisely one moveable stopper. In general, the moveable stopper can be coupled, for example, to an energy accumulator which can be selected from the group consisting of: a mechanical energy accumulator such as, for example, a spring element; a chemical energy accumulator; a physical energy accumulator such as, for example, a liquid gas and/or a medium which can carry out at least one phase transition, for example a liquid gas. Other configurations can also be conceivable.

The transport and transfer receptacle and/or the production method for producing same can be designed in such a manner that a separate tightness check may be unnecessary during and/or after production and can be omitted. A leakage can thus be identified solely by the fluid medium escaping during or after carrying out the charging of the fluid medium with positive pressure for example within a period of time of about 0 seconds to about 60 seconds after pressurization. The proposed method therefore differs from transport and transfer receptacles in which the pressurization does not take place until during the transfer of the fluid medium out of the container. The proposed method can therefore comprise, for example, an optical check in which it can be determined whether the fluid medium can emerge during or after pressurization. The production method can be carried out, for example, in such a manner that, after the method step has been carried out, a tightness check such as, for example, an optical tightness check, can be carried out, in order to detect emergence of the fluid medium. For example, the tightness check can be carried out within a time frame of at maximum of about one day, in one embodiment within a time frame of at maximum about 10 hours and, in another embodiment, of at maximum about 5 hours after the carrying out of the charging of the fluid medium with positive pressure has begun. A tightness check can generally be understood as meaning an operation in which it can be checked whether there is a non-intended emergence of fluid medium from an interior of the container. This can take place, for example, by optical detection of the fluid medium outside the container, for example by visible light, ultraviolet light or infrared light. For this purpose, for example, a visual check can be carried out by the manufacturer, for example by decanting staff in a decanting installation, or an automated optical check can take place, for example by a corresponding image identification device or similar devices. This can enable leakages to be identified early on, for example by untight transport and transfer receptacles being discarded before delivery to a retailer, a wholesaler or a customer. The user can also check the transport and transfer receptacle for irregularities, since an emergence of the fluid medium can also easily be determined with the naked eye. A higher safety and sterility level can therefore generally be achieved.

The production method can be carried out in such a manner that, after the charging of the fluid medium with positive pressure has been carried out, at least the at least one container and optionally one or more further parts of the transport and transfer receptacle can be accommodated in at least one packaging such as, for example, a blister pack. The packaging can, for example, be transported to the transport and transfer receptacle to a retailer, a wholesaler or a final customer. In one embodiment, the packaging can be at least partially designed as a sterile packaging, with at least one packaging interior which can be shielded under sterile conditions from the surroundings. In contrast to known transport and transfer receptacles, the container can therefore be accommodated in the packaging in a state charged with positive pressure, for example with a tensioned energy unit, such that, for example, transport of the container and/or storage of the container in the packaging can take place in a pressurized and tensioned state.

The energy unit can be a mechanical energy unit. The energy unit can be coupled, for example, mechanically to the container, for example by the energy unit acting mechanically on a stopper of the container. The energy unit can also be entirely, or partially, identical in terms of component parts to the container or parts of the container, for example by a stopper of the container itself being part of the energy unit, with, for example, a mechanical energy accumulator, for example at least one spring element, acting mechanically on the stopper.

The container can comprise at least one container wall with at least one (in one embodiment, only one) opening, wherein, after the introduction of the fluid medium has been carried out, the opening can be closed by at least one element with a perforable section such as, for example, by at least one perforable stopper. This can take place, for example, by the container being designed as a tubular container which can be open on one side, wherein, after the introduction of the fluid medium has been carried out, the opening on one side can be closed by the stopper. The perforable section such as the perforable stopper, can be designed so as to be displaceable relative to the container wall such as, for example, substantially parallel to an axis of the container, for example, to an axis of symmetry or axis of rotation of the container, which can be of tubular design in one embodiment.

The container can be at least partially accommodated in at least one external container, for example, after the introduction of the fluid medium has been carried out. The transport and transfer receptacle can thus furthermore have at least one external container in addition to the container and the energy unit. The external container, for example, can completely, or partially, surround the container. The container can be, for example, of at least partially tubular design. The external container can also be, for example, of at least partially tubular design and can surround the internal container, for example, concentrically. The energy unit can be at least partially arranged in an intermediate space between the external container and the container.

Charging the fluid medium with positive pressure, in particular the pressurization, can at least partially take place during connection of the external container to the container and/or during closing of the external container. The energy unit can be mechanically tensioned. This can take place, for example, in that, when the external container is connected to the container and/or during closing of the external container, the energy unit, for example at least one mechanical energy accumulator such as, for example, at least one spring element of the energy unit, can be acted upon in such a manner that the energy unit can be tensioned and/or the pressurization can take place simultaneously.

The energy unit can exert a pressure on at least one displaceable section of the container such as, for example, on a displaceable perforable section such as, for example, at least one perforable, displaceable stopper.

The energy unit can comprise a mechanical energy unit or can be completely designed as a mechanical energy unit, i.e. an energy unit which can affect the pressurization and/or an accumulation of energy in an exclusively mechanical way such as, for example, without electric or electromechanical components. The energy unit can be designed as a manually operable and manually tensionable energy unit. The energy unit can comprise at least one spring element such as, for example, at least one spiral spring and/or at least one helical compression spring.

If the energy unit comprises at least one spring element such as, for example, at least one spiral spring and/or at least one helical compression spring, then, after the charging of the fluid medium with positive pressure has been carried out, the spring element can press at least part of the container against at least one abutment of the transport and transfer receptacle. For example, the spring element can act on the container in such a manner that at least one displaceable section of the container such as, for example, a displaceable, perforable section such as, for example, a displaceable, perforable stopper which can close the container, can be pressed against the abutment. The container can be, for example, at least one tubular container which can open on one side and can be closed by a displaceably mounted stopper, with the tubular container which can be closed on one side being pressed, for example, by the stopper against the abutment. The abutment can generally be part of an external container at least partially surrounding the container. The external container can likewise be, for example, of at least partially tubular design. The spring element can be completely, or partially, accommodated, for example, in an intermediate space between the external container and the container. The abutment can generally be displaceable relative to the container during an emptying operation, in which the fluid medium can be removed from the container, for example during the transfer of the fluid medium out of the container. In particular, the abutment can penetrate the interior of the container during the emptying operation, for example by the abutment comprising a punch which can displace the stopper into the interior. The punch likewise can penetrate the interior.

The abutment, for example the punch, can comprise at least one perforation opening. At least one perforating element, such as, for example, at least one cannula, can penetrate through the perforation opening to at least one perforable section of the container such as, for example, at least one perforable stopper.

The energy unit can exert a substantially filling-level-independent pressure on the fluid medium during removal of the fluid medium within the scope of use of the transport and transfer receptacle. The energy unit, first of all, can exert an initial pressure on the fluid medium during the removal of the fluid medium. The pressure on the fluid medium during the removal operation cannot deviate by more than about 50% in one embodiment, by more than about 30% in another embodiment and, in yet another embodiment, by more than about 20% or even by more than about 10% from the initial pressure.

A supply method for supplying a fluid medium is proposed, wherein one or more fluid media can be supplied. Supplying can generally be understood as meaning an operation in which the at least one fluid medium can be made available at a use location and, in one embodiment, in a predetermined quantity and/or under sterile conditions. The supplying can take place, for example, after transport and/or storage. The supplying can take place, for example, to a device. The supply method may not comprise any therapeutic and/or surgical and/or diagnostic method steps which may be carried out on the human or animal body. However, the supply method itself can be part of a primary method which, in addition to the supply method, can comprise one or more therapeutic and/or surgical and/or diagnostic method steps which can be carried out on the human body or not on the human body.

The supply method can comprise the following method steps which can be in turn carried out in the sequence presented, but wherein, in turn, a different sequence can be also possible, analogously to the above description of the production method, and wherein also one or more additional method steps that are not mentioned can be carried out. A transport and transfer receptacle can be produced using a production method as claimed in one of the preceding claims. At least one perforable section can be perforated in order to produce a fluid connection between an interior of the container of the transport and can be transfer receptacle and an exterior for the purpose of removing the fluid medium from the container.

If, as explained above, the container can be accommodated in at least one packaging, then, before the perforating of the perforable section, the supply method can optionally comprise at least one further method step, in which the packaging can be entirely, or partially, opened and/or in which the container can be entirely, or partially, removed from the packaging. This opening and/or this removal can take place, for example, at least in such a manner that the perforable section can be accessible for perforating. For example, the step can comprise opening of a blister pack. Alternatively or in addition, during the perforating the at least one packaging can also be entirely, or partially, opened at the same time and/or perforated at the same time.

This perforable section, as explained above, can comprise at least one perforable wall of the container such as, for example, at least one perforable stopper such as, for example, a perforable stopper mounted displaceably in the container. With regard to possible configurations, reference can be made to the above description of the production method. The perforable section can have elastic properties, for example, by one or more elastomer materials being used. Perforating can generally be understood as meaning an operation in which the perforable section can be penetrated by at least one perforating element such as, for example by at least one needle element, thus producing a fluid connection, for example by a hollow perforating element such as, for example, a cannula, being used. The perforating preferably can take place reversibly, and therefore, after the perforating element has been removed from the perforable section such as, for example, the perforable stopper, the opening produced in the process can be closed again. This can also enable the fluid medium to be removed little by little, for example, in constant or else variable portions.

A fluid connection can generally be understood as meaning a connection through which fluid medium can pass out of the interior of the container into an exterior such as, for example, an exterior outside the transport and transfer receptacle.

The supply method can furthermore comprise a transfer of at least part of the fluid medium out through the fluid connection. The transfer can be completely, or partially, driven by the energy unit. The energy unit can thus charge, for example, the fluid medium with pressure in such a manner that the fluid medium can be driven out of the container via the fluid connection.

The transfer can be effected completely by energy accumulated in the energy unit in charging the fluid medium with positive pressure such as, for example, mechanical energy, and therefore, for example, no additional energy that has not been accumulated in the energy unit can be introduced into the transport and transfer receptacle during the transfer.

The supplying can at least partially take place into an injection cannula. By the injection cannula, the fluid medium can be supplied, for example, to a further device or else can be used within the scope of a primary method, for example an injection method. In one configuration of the supply method, supplying can at least partially take place into at least one receptacle which can be formed separately from the transport and transfer receptacle. This may involve, for example, a bottle, a screw cap jar, a snap cap jar or another suitable type of receptacle.

In a further embodiment of the supply method, the supply method can be carried out repeatedly, wherein the perforable section of a plurality of containers can be perforated successively in order to produce a fluid connection between an interior of the containers and an exterior for the purpose of removing the fluid medium from the containers, wherein the containers can be changed without admitting gas bubbles. In this manner, for example, a first transport and transfer receptacle can be produced, then perforating of at least one perforable section for producing a fluid connection between an interior of the container of the first transport and transfer receptacle and an exterior for the purpose of removing the fluid medium from the first container can take place. At the same time, overlapping in time or subsequently, at least one further transport and transfer receptacle can be produced, followed by perforating of at least one perforable section in order to produce a fluid connection between an interior of the container of the further transport and transfer receptacle and an exterior, for the purpose of removing the fluid medium from the further container. Changing of the containers can take place, for example, without admitting gas bubbles into a system which uses the transport and transfer receptacle.

The supply method can take place in particular in such a manner that the supplying at least partially takes place into at least one flexible connection such as, for example, a flexible fluid connection such as, for example, into at least one tubing connection. For example, the supply method can take place into a tubing connection of an infusion kit. The flexible connection into which the supply method can take place can thus open into at least one infusion kit, wherein the infusion kit can comprise at least one infusion cannula and at least one plaster. The infusion cannula can be used, for example, in a primary infusion method, which can include the supply method, to inject the fluid medium into a body tissue of a user.

The supply method can furthermore be carried out in such a manner that the supply method can comprise at least one interruption step. The perforating of the perforable section can be stopped in the interruption step and the fluid connection can thereby be interrupted. For example, this can take place by the perforable section having flexible properties. For example, a perforating element can be pulled out of the perforable section or removed in another manner, wherein a remaining opening can be closed because of the flexible properties of the perforable element and the fluid connection can be interrupted. This can take place, for example, by using a perforable, flexible stopper. As explained above, an advantage of the transport and transfer receptacle and also of the supply method described can be that the pressurization of the fluid medium in the container can take place independently of the production of the fluid connection such as, for example, in a mechanically decoupled manner. For example, the pressurization can continue, whereas the production of the fluid connection can be produced, for example, exclusively by the perforating, which can be mechanically decoupled from the pressurization and which can be, for example, reversible. Thus, for example with a positive pressure being maintained in the container, the fluid connection can be produced and optionally interrupted again in order subsequently optionally to be restored one or more further times, for example, by renewed perforating.

As explained above, the supply method can be designed in such a manner that the supplying does not comprise any therapeutic, diagnostic or surgical method step carried out on a human or animal body. However, the supply method can be part of a primary injection method which can comprise at least one supply method according to one or more of the above-described configurations. Furthermore, the injection method can comprise at least one injection step, wherein the fluid medium supplied by the supply method can be injected into a body tissue of a human or animal body.

The supply method, as explained above, can comprise at least one perforating of at least one perforable section in order to produce a fluid connection between the interior of the container and the exterior, for the purpose of removing the fluid medium from the container. In the supply method, use can be made of at least one perforating element such as, for example, at least one cannula, for producing the fluid connection. The perforating element can have a point, for example, at an end pointing toward the container, by the perforable section, for example the perforable stopper, can be perforated. However, the perforating element may optionally also comprise a point such as, for example, an injection needle and, for example, an injection cannula at an end facing away from the container. The injection needle can be used for injecting the fluid medium into the body tissue. The perforating element can comprise an injection needle such as, for example, an injection cannula, with two points arranged at opposite ends, for example one point which can point towards the container and one point which can point toward the body tissue into which the injection can be intended to take place.

The perforating element can therefore be designed as an injection needle and/or used as an injection needle. Alternatively or in addition, however, the perforating element can also be connected to at least one injection element such as, for example, an injection cannula, via at least one flexible connection, for example, via at least one tubing connection such as, for example, via at least one sterile tubing connection. The perforating can thus be designed, for example, to be spatially separate from the actual injection into the body tissue, for example, at a distance of at least about 5 cm in one embodiment, at least about 10 cm in another embodiment, at least about 20 cm in another embodiment and at least about 50 cm in yet another embodiment. Separate elements can thus be used for the perforating and for the injection such as, for example, separate cannula which can be connected to each other via the at least one flexible connection.

The injection method can transfer the fluid medium out of the container and the injection step can be carried out spatially separately from each other. In particular, a spatial separation of at least about 30 mm in one embodiment, of at least about 50 mm in another embodiment, and of at least one 100 mm can occur in yet another embodiment, for example the above-described spatial separation with the abovementioned preferred distances between the perforating and the injection.

Furthermore, the injection and the perforating can also be configured separately in time from each other, for example, in contrast to conventional injection methods by syringes or autoinjectors. For example, at least one injection element can be inserted into the body tissue and subsequently, with a time delay, the fluid medium can be transferred out of the container into the body tissue, for example with a time delay of at least about 5 seconds in one embodiment or of at least about 10 seconds in another embodiment. In principle, a different configuration of a separation in time between transfer of the fluid medium out of the container and insertion into the body tissue can also be possible.

The injection method can furthermore be carried out in such a manner that insertion of at least one injection element into the body tissue and the transfer of the fluid medium out of the container are separate working steps, preferably separate working steps which are mechanically decoupled from each other. As explained above, said decoupling can take place, for example, via the at least one optional flexible connection, in particular via the at least one optional tubing connection and, particularly preferably, via the at least one sterile tubing connection.

A transport and transfer receptacle for storing and supplying at least one fluid medium is proposed. The transport and transfer receptacle can be stored and supplied at least one sterile liquid such as, for example, a diagnostic agent and/or therapeutic agent. For a definition of the term of transport and transfer receptacle and with regard to possible configurations of same, reference can be made to the above description of the production method. However, in principle, other configurations can also be possible. The transport and transfer receptacle can be producible according to a production method as per one or more of the above-described configurations or as per one or more of the examples still to be described below.

The transport and transfer receptacle can comprise at least one container for receiving the fluid medium. The container can have a container wall and at least one perforable section such as, for example, at least one perforable stopper, wherein, by perforating the perforable section, a fluid connection can be produced to an interior of the container for the purpose of removing the fluid medium from the container and at least one energy unit such as, for example, an integrated energy unit. The energy unit can affect—for example, complete—emptying of the fluid medium from the container when the transport and transfer receptacle is used. The energy unit can charge the fluid medium in the container with positive pressure. The positive pressure can be maintained and/or is maintained until the fluid medium is removed. The transport and transfer receptacle furthermore can have at least one packaging. At least the container can be received in the state charged with positive pressure in the packaging.

The transport and transfer receptacle can be configured so that the fluid medium can come into contact exclusively with a container wall of the container and a closure element of the container during transport and storage.

With regard to possible configurations of the packaging, reference can be made to the above description of the optional configurations of the production method.

The energy unit can act mechanically on the perforable section. The perforable section can be entirely, or partially, identical to a closure element, for example, to a stopper such as, for example, a perforable stopper accommodated displaceably in the container. The energy unit can therefore also act mechanically on the closure element. A mechanical action can generally be understood as meaning a charging with a force in such a manner that the perforable section and the closure element can be moved. The perforable section and/or the closure element can comprise one or more stoppers, for example one or more perforable stoppers. The energy unit can thus mechanically act on the stopper such as, for example, the perforable stopper.

One configuration in which the fluid medium can come into contact exclusively with the container wall and the closure element of the container can be understood as meaning a configuration in which the fluid medium, before use thereof, at maximum can come into contact with the elements and/or surfaces which define and delimit the interior of the container. For example, the fluid medium may accordingly not be in contact with valves, tubings or other fluidic elements.

With regard to possible configurations of the container, reference can be made to the above description. A container wall can generally be understood as meaning an inside of the container, which inside can face the interior and can have, for example, at least one cylindrical section and/or at least one flat section, if the container is of tubular design. A closure element can generally be understood as meaning an element which can close the container, as described above. For example, the closure element can comprise a stopper and/or can be a stopper and/or can comprise a perforable closure element such as, for example, a perforable stopper. The fluid medium can thus come into contact, for example, exclusively with the container wall and the stopper before the stopper is removed from the interior.

The container and optionally one or more further parts of the transport and transfer receptacle can be entirely, or partially, accommodated in at least one packaging.

The packaging can be part of the transport and transfer receptacle, even if the packaging can be entirely, or partially, removed, for example, before use of the transport and transfer receptacle and/or before removal of the fluid medium. The remaining parts of the transport and transfer receptacle, with the exception of the packaging, can thus form at least one use unit which, for example after opening and/or complete or partial removal of the packaging, can be used for removal of the fluid medium. For example, all of the components of the transport and transfer receptacle, with the exception of the packaging, can be accommodated in one and the same packaging. An external container which can entirely, or partially, surround the container and optionally the energy unit can also be accommodated in the packaging. The packaging can be or can comprise an air-tight and/or germ-proof packaging. At least partial accommodating of the container and optionally of one or more further components of the transport and transfer receptacle in the packaging can be understood generally as meaning, for example, a configuration in which at least one region of the abovementioned component which can be accommodated in the packaging and, in one embodiment, the entire component, can be covered by the packaging. For example, at least the container and optionally, furthermore, the energy unit can be in each case completely, or partially, covered by the same packaging, whereas further components can optionally also be supplied and/or packaged separately. The container and the energy unit can be accommodated together in a packaging. For example, the container and optionally the energy unit can be accommodated in the packaging in a state in which the fluid medium can be charged with positive pressure in the container by the energy unit. Therefore, for example, a mechanical energy accumulator of the energy unit, for example at least one spring element can be accommodated in a tensioned state in the packaging.

The transport and transfer receptacle can be designed in particular in such a manner that the fluid medium can be accommodated therein in a manner free from bubbles. Bubble-free accommodation can be understood as meaning a configuration in which the fluid medium does not contain any gas bubbles and may not be in contact with gas bubbles as long as the fluid medium can be accommodated in the container. Gas bubbles here can generally be understood as meaning cohesive volumes of gas with a volume of at least about $5 \times 10^{-7}$ mm$^3$.

The container can be designed in such a manner that the container may not have a fluid connection between the interior of the container and an exterior, with the exception of the fluid connection which can be produced by perforating the perforable section, for example exclusively for removing the fluid medium. The container can be configured in such a manner that no valves or similar fluid connections can be provided.

Complete emptying of the fluid medium can be understood as meaning emptying of the container to the effect that, when a fluid connection is produced between an exterior and the interior of the container, when the perforable section is perforated, and when the fluid connection is maintained solely on the basis of the energy unit and, for example, the mechanical energy accumulated in the energy unit, an emptying of the container occurs, in which at least about 90% of the fluid medium which was previously contained in the container is removed from the container in one embodiment, at least about 95% in another embodiment and at least about 98% in yet another embodiment. For example, residual quantities which do not exceed about 10% of the original fluid volume in one embodiment, do not exceed about 5% in another embodiment and, in yet another embodiment, do not exceed about 2% or even about 1%, can be tolerated in the container.

The energy unit can act mechanically on the displaceable section, for example on a perforable or non-perforable, displaceable section. This can take place, for example, by the energy unit, as described above, charging the displaceable section with a force which can have at least one force component toward the interior of the container. For example, the displaceable section can be pushed towards the interior of the container. This can take place, as explained above, for example by the energy unit comprising at least one spring element, for example a spiral spring and/or at least one helical compression spring, which can act directly or indirectly on the displaceable section in such a manner that the latter can be charged with the abovementioned force. This can take place, for example, by the spring element acting directly on the displaceable section or by the spring element acting on the container in such a manner that the displaceable section can be pressed, for example, against an abutment. As described above, the displaceable section can comprise at least one displaceable stopper, for example, a perforable, displaceable stopper, which can be mounted movably in the container. The energy unit can be configured in particular in such a manner that the mechanical action can exist continuously after production of the transport and transfer receptacle until an intended use of same and complete or partial removal of the fluid medium from the container.

The transport and transfer receptacle can producible according to a production method as per one or more of the configurations described above or yet to be described below. The perforable section can therefore comprise at least one, or in one embodiment exactly one, stopper which can be mounted displaceably with respect to a container wall of the container, or can be one stopper which can be mounted displaceably relative to the container wall. As explained above, the container wall can be, for example, of substantially tubular design, for example with a cylindrical inner wall. The container can thus be, for example, in the form of a tube which can be closed on one side, wherein an opening located opposite the closed end can be closed, for example, by the stopper. In general, the container can therefore be a tubular container provided with an opening on one side.

After reception in the container, the fluid medium can be in contact exclusively with the container wall and the perforable section. For example, the transport and transfer receptacle can be designed in such a manner that the fluid medium can exclusively be in contact with the two elements mentioned, i.e., for example, exclusively with the container wall and the stopper, but not with further elements, such as, for example, valves, tubing connections or similar elements, up to the time at which the fluid medium is transferred out of the container.

The transport and transfer receptacle can be designed in such a manner that the receptacle, and in particular the container, may not have any valves. The transport and transfer receptacle can be configured, in such a manner that, before the perforable section can be perforated, the container may not have a fluid connection between an interior receiving the fluid medium and the container and a surroundings of the container. The transport and transfer receptacle can be designed in such a manner that the fluid connection can be produced exclusively by perforating the perforable section, at least for a nondestructive use of the transport and transfer receptacle.

The energy unit can be designed to maintain the positive pressure after production of the transport and transfer receptacle during storage of the transport and transfer receptacle for a period of time of at least two weeks, of at least three weeks, at least four weeks, at least one month, at least two months, at least one year or even at least several years, at a pressure level of at least about 50% in one embodiment, at least about 70% in another embodiment and, in yet another embodiment, of at least about 80% of an initial pressure. This can take place by a corresponding configuration of a spring element. The spring element can be configured, for example, with a low hysteresis and a corresponding, permanent rigidity which can be produced, for example, by a corresponding choice of material or a corresponding geometry of the spring element. Furthermore, the maintaining of the pressure level can also be assisted, for example, by a corresponding tightness of the container.

The container of the transport and transfer receptacle, wherein one or more containers of this type can be provided, can be completely, or partially, filled with the fluid medium. This can take place, for example, in such a manner that a gas bubble originally present in the fluid medium has completely dissolved after a residence period, for example a residence period of one to three days. The dissolution can take place, for example, by corresponding gas solubility which is customarily a function of the temperature and the pressure, for example, the pressure by means of which the fluid medium can be charged in the container by the energy unit.

The energy unit can comprise at least one spring element. The spring element can act directly, or indirectly, on the perforable section. Action can be understood in particular as meaning charging the perforable section with a force, for example, charging with a force having at least one force component toward the interior of the container. The charging with force can take place directly, or indirectly, for example by the spring element pressing directly on the perforable section and/or by the spring element pressing the perforable section against at least one abutment. The pressing can in turn take place directly or indirectly, for example by the spring element acting on the container, for example a container wall. The perforable section can be pressed via the container wall in turn against the abutment.

The container and, in one embodiment, the entire transport and transfer receptacle can be free from electric components. For example, the transport and transfer receptacle can be completely designed as a mechanical unit.

Furthermore, the transport and transfer receptacle can comprise at least one external container which, for example, can likewise be entirely, or partially, accommodated in the at least one packaging. For example, the external container can be designed in such a manner that the container can be at least partially accommodated in the external container. The energy unit can be at least partially arranged in an intermediate space between the external container and the container, for example in at least one annular gap between the external container and the container. This can take place, for example, by the energy unit comprising at least one spring element such as, for example, at least one spiral spring and/or at least one helical compression spring. The spring element can be accommodated, for example, in the annular gap. The external container can surround the container at least partially in a tubular manner. The external container and the energy unit can be configured in such a manner that, during connection of the external container to the container and/or during closing of the external container, the fluid medium can be pressurized. The energy unit can be mechanically tensioned. The closing and/or connection can take place, for example, by one or more connecting elements, for example, by producing at least one positive and/or non-positive and/or integrally bonded connection. Screw connections, latching connections or similar connections can be used. The external container and/or the container can have one or more connecting elements. The external container can have at least two container parts which can be connected to each other. The transport and transfer receptacle can be configured in such a manner that, when the at least two container parts are connected, the energy unit can be mechanically tensioned. This can take place, for example, by the energy unit having at least one spring element which can be accommodated in the external container, for example in an intermediate space between the external container and the container. When the container parts are connected, the volume of an interior of the external container can be reduced, and therefore the spring element can be, for example, compressed and can thereby be mechanically tensioned. The at least two container parts can be connected via a connection selected from a screw connection and a latching connection. However, other connections can also be possible.

The energy unit can be a purely mechanical energy unit without electric and/or electromechanical components, for example, a manually operable energy unit, but a manually operable energy unit which, however, can be tensionable automatically, for example automatically on closing of the external container and/or when the external container is connected to the container. A purely mechanical energy unit can be understood as meaning an energy unit in which the pressurization and/or the accumulation of energy can take place in a purely mechanical way, for example via one or more purely mechanical spring elements for pressurization and/or accumulation of energy.

As likewise explained above, the energy unit can thus comprise at least one spring element such as, for example, at least one spiral spring and/or at least one helical compression spring. The spring element can be produced from a metallic material such as, for example, from spring steel. In principle, however, alternatively or in addition, the use of other types of materials, such as materials having a high degree of elasticity, for example the use of one or more elastomer materials, can also be possible. The spring element can press at least part of the container such as the perforable section, against at least one abutment of the transport and transfer receptacle. For example, this abutment can be part of an external container which completely, or partially, surrounds the container. The spring element can act on the container in such a manner that at least one displaceable, perforable stopper can be pressed against the abutment. For this purpose, the spring element, for example, can press the abutment against the perforable stopper and/or can charge the container with a force in such a manner that the perforable stopper can be pressed against the abutment. Combinations of the possibilities mentioned can also be conceivable.

The abutment can be part of an external container at least partially surrounding the container. The abutment can be displaceable relative to the container during an emptying operation, in which the fluid medium can be removed from the container, and can penetrate an interior of the container. The abutment can thus comprise, for example, a punch which can be of smaller dimensions in terms of the outside diameter thereof than an inside diameter of the container and which can act on the perforable stopper. The abutment can comprise at least one perforation opening, wherein at least one perforating element, such as at least one cannula, can penetrate through the perforation opening to the at least one perforable section of the container, for example, to the at least one perforable stopper. The abutment can thus be designed, for example, as a punch, wherein the perforation opening can have, for example, a channel in the punch, for example a central channel, such as a channel which can be oriented substantially parallel to an axis of the container, for example an axis of rotation. Generally, in this configuration or other configurations, the container can be mounted relative to the optional external container. The container can thus be displaced relative to the external container, for example during the emptying operation.

The perforating element can be part of the transport and transfer receptacle. The transport and transfer receptacle can thus generally comprise at least one perforating element for perforating the at least one perforable section, for example a perforating element which can be mounted movably relative to the container in an external container of the transport and transfer receptacle and/or is mounted movably relative to the optional external container. The perforating element can be driven, for example, manually or in another manner in order to carry out the perforating. In general, the transport and transfer receptacle can therefore comprise at least one perforating element which can be mounted movably, in particular displaceably, in the transport and transfer receptacle, such as displaceably in an external container which completely, or partially, surrounds the container.

The energy unit can exert a substantially filing-level-independent pressure on the fluid medium during removal of the fluid medium within the scope of use of the transport and transfer receptacle.

The transport and transfer receptacle can generally have at least one perforating element for perforating the perforable section, such as at least one cannula. This perforating element can also be entirely, or partially, accommodated in the packaging. For example, this perforating element can be completely, or partially, mounted in an interior of an external container, such as displaceably, wherein the external container, for example, can completely, or partially, surround the container.

The transport and transfer receptacle can furthermore comprise at least one injection element, such as at least one injection cannula, wherein the injection element can be inserted into a human or animal body tissue and/or into a vessel formed separately from the container, such as into a receptacle and/or another type of fluid unit. This injection element can also be entirely, or partially, accommodated in the packaging. A use example which can be mentioned is the dissolution of one or more substances, for example freeze-dried medicaments, which can be accommodated in the vessel and can be dissolved by at least one solvent supplied by the transport and transfer receptacle. For example, one or more freeze-dried medicaments can be dissolved by sterile water (e.g. what is referred to as "water for injection") before use.

The injection element and the perforating element can be connected to each other, such as fluidically. The perforating element and the injection element can thus be rigidly connected to each other, for example by the elements involving mutually opposite ends of an injection cannula, which ends can be both of pointed or sharp design in order to be able to affect the perforating or the injection. Alternatively or in addition, however, a different type of connection can also be conceivable, for example a tubing connection, a connection via a tube or a different type of fluidic connection. In general, the connection can be selected from the group comprising: a rigid connection, wherein the perforating element and the injection element can be formed at mutually opposite ends of the rigid connection, for example, in the form of mutually opposite ends of an injection needle which can be pointed or sharpened at both ends; a flexible connection such as, for example, a tubing connection, such as, for example, a sterile tubing connection.

The injection element can comprise an infusion kit with at least one cannula and at least one plaster. For example, the cannula can be arranged substantially perpendicularly or at least obliquely to a plaster surface which can be stuck onto a skin surface of a patient.

The transport and transfer receptacle can be designed in such a manner that producing a fluid connection between the injection element and the interior and inserting the injection element into the human or animal body tissue and/or into the vessel can be formed separately from the container form separate working steps.

The transport and transfer receptacle can have at least one coupling. The coupling can be coupled to at least one vessel formed separately from the transport and transfer receptacle. A coupling can generally be understood as meaning a mechanical connecting element which can produce a connection of this type, such as for producing a non-positive and/or positive connection. For example, the coupling can have a clamping connection, a screw connection or a latching connection. A vessel can generally be understood as meaning a device which can be configured for receiving one or more fluid media, for example for storing, for transporting or for conducting fluid media. The vessel can comprise at least one receptacle formed separately from the transport and transfer receptacle and/or at least one different type of device formed separately from the transport and transfer receptacle. The coupling can enable transfer of the fluid medium out of the container of the transport and transfer receptacle into the vessel coupled thereto. The vessel can contain, for example, one or more substances, for example in solid form, which can be dissolved and/or suspended and/or emulsified by the at least one fluid medium supplied by the transport and transfer receptacle. The vessel can contain, for example, at least one freeze-dried substance, for example at least one freeze-dried medicament, which can be dissolved before use.

The transport and transfer receptacle can furthermore in general be designed in such a manner that it can have at least one switching element. The switching element can be configured in particular in order, in at least one first switch position, to maintain the fluid connection to the interior of the container by perforating the perforable section. Furthermore, the switching element can be configured in such a manner that, in at least one second switching position, the switching element can interrupt the fluid connection by interrupting the perforating of the perforable section. The switching element can thus be designed, for example, as a purely mechanical switching element. The switching element can act directly, or indirectly, on at least one perforating element of the transport and transfer receptacle in order to effect and/or to interrupt the perforating. The perforating element can thus comprise, for example, at least one needle such as, for example, at least one cannula, which can be mounted displaceably in the transport and transfer receptacle. The switching element can be configured, for example, in order to effect the displacement and, in the first switch position, to supply a perforated state of the perforable section and therefore to produce the fluid connection, and, in at least one second position, to interrupt the fluid connection, for example by the perforable element being completely, or partially, pulled out of the perforable section. The change between the switch positions can take reversibly. For example, the switching element can be repeatedly moved to and fro between the at least one first switch position and the at least one second switch position or vice versa. This can take place by a simple linear action on the perforating element. The switching element can be designed in such a manner that it can be accessible from the outside for a user without the transport and transfer receptacle having to be opened. For example, the transport and transfer receptacle can have at least one external container, wherein the container can be completely, or partially, arranged in the external container, wherein the perforating element can completely, or partially, be accommodated in the external container, and wherein the switching element can permit and/or drive a relative movement between the perforating element and the external container. For example, the perforating element can be mounted movably, such as, for example, displaceably, in the external container, wherein the movement, such as the displacement, can be driven by a user by the at least one switching element or part of same, for example by a handle and/or button accessible from the outside.

The energy unit can be actuatable independently of the perforating of the perforable section in order to decouple the charging of the fluid medium with positive pressure spatially and/or in time from the production of the fluid connection. This can take place, for example, in such a manner that the energy unit can act mechanically directly, or indirectly, on the perforable section in order to effect the pressurization. The perforating of the perforable section can be realizable, for example, independently therefrom and without influencing the pressurization.

The transport and transfer receptacle can be entirely, or partially, accommodated in at least one packaging.

A production method for producing a transport and transfer receptacle for at least one fluid medium, such as, for example, for at least one sterile liquid comprises supplying at least one container for receiving the fluid medium. The container can have a closure element such as, for example, at least one perforable closure element such as, for example, a perforable stopper. At least one energy unit such as, for example, an integrated energy unit, can be supplied. The energy unit can affect the complete emptying of the fluid medium from the container when the transport and transfer receptacle is used. The fluid medium can be introduced into the container and the container can be closed with, for example, a displaceable stopper. The fluid medium can be charged with a positive pressure by using the energy unit, for example. The positive pressure can be maintained until the fluid medium is removed.

The production method can further comprise packing at least the container in the state charged with positive pressure in at least one packaging.

After the charging of the fluid medium with positive pressure has been carried out, the transport and transfer receptacle can be stored for a period of time of at least two weeks in one embodiment and of at least three weeks in another embodiment.

In the introduction of the fluid medium, first of all at least one gas bubble can be produced in the container. The charging of the fluid medium with positive pressure can be carried out in such a manner that the gas bubble can completely disappear after a waiting period. The waiting period can be of at least one hour in one embodiment and in another embodiment can be at least two hours. A transport and transfer receptacle free from gas bubbles can be the result.

The production method can be carried out before the transport and transfer receptacle is sold to a customer such as, for example, a final customer.

In the charging of the fluid medium with positive pressure, at least one spring element of the transport and transfer receptacle can be tensioned. The spring element can act on at least one displaceable section of the container such as, for example on at least one stopper such as, for example, on at least one perforable stopper.

The charging of the fluid medium with positive pressure can be carried out in such a manner that the positive pressure can adopt at least a pressure level required for transfer of the fluid medium out of the container.

The container is configured in such a manner that, after the charging of the fluid medium with positive pressure has been carried out and before the removal, the fluid medium can be in contact exclusively with a container wall of the container and a perforable section of the container such as, for example, a perforable stopper.

After the charging of the fluid medium with positive pressure has been carried out, the container may not have a fluid connection between an interior of the container, the interior receiving the fluid medium, and a surroundings of the container.

The container can have at least one perforable section through which the fluid medium can be removed after the perforable section is perforated.

The container such as, the transport and transfer receptacle, can be free from electric components.

After the charging of the fluid medium with positive pressure has been carried out, a tightness check such as, for example, an optical check, can be carried out. A possible escape of the fluid medium as a consequence of the positive pressure can be detected as a consequence of a leakage from the container.

After the charging of the fluid medium with positive pressure has been carried out, the transport and transfer receptacle can be accommodated in at least one packaging such as, for example, a blister pack.

The energy unit can be mechanically coupled to the container.

The container can comprise a container wall with an opening. After the introduction of the fluid medium has been carried out, the opening can be closed by at least one element with a perforable section such as, for example by at least one perforable stopper.

The container can be a tubular container which can be open on one side.

The perforable section such as, for example, the perforable stopper, can be displaceable relative to the container wall such as, for example, substantially parallel to an axis of the container.

The container can be at least partially accommodated in at least one external container, such as, for example, after the introduction of the fluid medium has been carried out.

The energy unit can at least partially be arranged in an intermediate space, between the external container and the container.

The charging of the fluid medium with positive pressure can at least partially take place during connection of the external container to the container and/or during closing of the external container. The energy unit can be mechanically tensioned.

The energy unit can exert a pressure on at least one displaceable section of the container such as, for example, on a displaceable, perforable section such as, for example, on a perforable, displaceable stopper.

The energy unit can comprise a mechanical energy unit and can be designed as a purely mechanical energy unit without electric or electromechanical components.

The energy unit can comprise at least one spring element such as, for example, at least one spiral spring and/or at least one helical compression spring.

After the charging of the fluid medium with positive pressure has been carried out, the spring element can press at least part of the container against at least one abutment of the transport and transfer receptacle.

The spring element can act on the container in such a manner that at least one displaceable section of the container such as, for example a displaceable, perforable section such as, for example, a displaceable, perforable stopper which can close the container, can be pressed against the abutment.

The abutment can be part of an external container at least partially surrounding the container.

The abutment can be displaceable relative to the container during an emptying operation, in which the fluid medium can be removed from the container and can penetrate an interior of the container.

The abutment can comprise at least one perforation opening. At least one perforating element such as, for example, at least one cannula, can penetrate through the perforation opening to at least one perforable section of the container such as, for example, to at least one perforable stopper.

The energy unit can exert a substantially filling-level-independent pressure on the fluid medium during removal of the fluid medium within the scope of use of the transport and transfer receptacle.

A supply method for supplying a fluid medium can comprise producing a transport and transfer receptacle using the production method and perforating at least one perforable section in order to produce a fluid connection between an interior of the container and an exterior for the purpose of removing the fluid medium from the container.

The supply method can further comprise a transfer of at least part of the fluid medium by the fluid connection. The transfer can completely or partially be driven by the energy unit.

The transfer can be completely effected by energy accumulated in the energy unit in the charging of the fluid medium with positive pressure such as, for example, mechanical energy.

The supplying at least partially can take place into an injection cannula.

The supplying can at least partially take place into at least one receptacle formed separately from the transport and transfer receptacle.

The supply method can be carried out repeatedly. The perforable section of a plurality of containers can be successively perforated in order to produce a fluid connection between an interior of the container and an exterior for the purpose of removing the fluid medium from the containers. The containers can be changed without gas bubbles being admitted.

The supplying at least partially can take place into at least one flexible connection such as, for example, into at least one tubing connection.

The flexible connection can open into at least one infusion kit. The infusion kit can comprise at least one infusion cannula and at least one plaster.

The supply method can further comprise at least one interruption step, wherein the perforating of the perforable section can be stopped in the interruption step and the fluid connection can be interrupted.

An injection method for injecting at least one fluid medium can comprise the supply method and at least one injection step, wherein the fluid medium supplied by the supply method can be injected into a body tissue of a human or animal body.

At least one perforating element such as, for example, a cannula, can be used for producing the fluid connection.

The perforating element can comprise an injection needle such as, for example, an injection cannula, at an end facing away from the container. The injection needle can be used for injecting the fluid medium into the body tissue.

The perforating element can comprise an injection needle such as, for example, an injection cannula, with two points arranged at mutually opposite ends.

The perforating element can be connected to at least one injection element such as, for example, to an injection cannula, via at least one flexible connection such as, for example via at least one tubing connection such as, for example, at least one sterile tubing connection.

The transfer of the fluid medium out of the container and the injection step can be carried out spatially separately from each other such as, for example with a spatial separation of at least about 30 mm in one embodiment, with a spatial separation of at least about 50 mm for example, and, in yet another embodiment, with a spatial separation of at least about 100 mm.

First of all at least one injection element can be inserted into the body tissue and, subsequently, with a time delay, the fluid medium can be transferred out of the container into the body tissue with a time delay of at least about 5 seconds in one embodiment and of at least about 10 seconds in another embodiment.

Insertion of at least one injection element into the body tissue and transfer of the fluid medium out of the container can be separate working steps such as, for example, separate working steps decoupled mechanically from each other.

A transport and transfer receptacle for storing and supplying at least one fluid medium such as, for example, for storing and supplying at least one sterile liquid can comprises at least one container for receiving the fluid medium. The container can have a container wall and at least one perforable section such as, for example, a perforable stopper. By perforating the perforable section, a fluid connection can be produced to an interior of the container for the purpose of removing the fluid medium from the container. The transport and transfer receptacle can also comprise at least one energy unit such as, for example an integrated energy unit. The energy unit can affect complete emptying of the fluid medium from the container when the transport and transfer receptacle is used. The energy unit can charge the fluid medium in the container with positive pressure. The positive pressure can be maintained until the fluid medium is removed. The transport and transfer receptacle can furthermore have at least one packaging. At least the container in the state charged with positive pressure can be received in the packaging.

The transport and transfer receptacle can be produced according to the production method.

The perforable section can comprise a stopper mounted displaceably relative to a container wall of the container and can be one stopper mounted displaceably relative to the container wall.

The transport and transfer receptacle and the container may not have any valves.

Before perforating of the perforable section, the container may not have a fluid connection between an interior of the container, the interior receiving the fluid medium, and surroundings of the container.

The fluid connection can be produced exclusively by perforating the perforable section.

The energy unit can maintain the positive pressure after production of the transport and transfer receptacle during storage of the transport and transfer receptacle for a period of time of at least two weeks in one embodiment or of at least three weeks in another embodiment, such that at a pressure level of at least about 50% in one embodiment, at least about 70% in another embodiment and, in yet another embodiment, at least about 80% of an initial pressure.

The energy unit can comprise at least one spring element acting on the perforable section.

The container, such as the transport and transfer receptacle, can be free from electric components.

The transport and transfer receptacle can furthermore comprise at least one external container. The container can at least partially be accommodated in the external container.

The energy unit can at least partially be arranged in an intermediate space between the external container and the container.

The external container can surround the container at least partially in a tubular manner.

The external container and the energy unit can be configured in such a manner that the fluid medium can be pressurized during connection of the external container to the container and/or during closing of the external container. The energy unit can be mechanically tensioned.

The external container can have at least two container parts which can be connected to each other. The transport and transfer receptacle can be configured in such a manner that the energy unit can be mechanically tensioned when the container parts are connected.

The container parts can be connected via a connection selected from a screw connection and a latching connection.

The energy unit can be a purely mechanical energy unit without electric and/or electromechanical components such as, for example, a manually operable, but automatically tensionable energy unit.

The spring element can press at least part of the container such as, for example, the perforable section such as, for example, the perforable stopper, against at least one abutment of the transport and transfer receptacle.

The spring element can act on the container in such a manner that at least one displaceable, perforable stopper can be pressed against the abutment.

The perforating element can be part of the transport and transfer receptacle.

The perforating element can be mounted displaceably in the transport and transfer receptacle such as, for example, displaceably in an external container.

The energy unit can exert a substantially filling-level-independent pressure on the fluid medium during removal of the fluid medium within the scope of use of the transport and transfer receptacle.

The transport and transfer receptacle can comprise at least one perforating element such as, for example, a cannula for perforating the perforable section.

The transport and transfer receptacle can furthermore comprise at least one injection element such as, for example, an injection cannula. The injection element can be inserted into a human or animal body tissue and/or into a vessel formed separately from the container.

The perforating element and the injection element can be connected to each other.

The connection can be selected from the group comprising a rigid connection, wherein the perforating element and the injection element can be formed at mutually opposite ends of the rigid connection or a flexible connection such as, for example, a tubing connection such as, for example, a sterile tubing connection.

The injection element can comprise an infusion kit with a cannula and a plaster.

The transport and transfer receptacle can be designed in such a manner that producing a fluid connection between the injection element and the interior and inserting the injection element into the human or animal body tissue and/or into the vessel formed separately from the container can form separate working steps.

The transport and transfer receptacle can have at least one coupling. The coupling can be coupled to at least one vessel formed separately from the transport and transfer receptacle such as to at least one receptacle formed separately from the transport and transfer receptacle and/or to at least one device formed separately from the transport and transfer receptacle. The fluid medium can be transferred from the container of the transport and transfer receptacle into the vessel coupled thereto.

The transport and transfer can have at least one switching element. The switching element can be configured in order, in at least one first switch position, to maintain the fluid connection to the interior of the container by perforating the perforable section. The switching element can furthermore be configured in order, in at least one second switch position, to interrupt the fluid connection such as by interrupting the perforating of the perforable section.

The energy unit can be actuable independently of the perforating of the perforable section in order to decouple the charging of the fluid medium with positive pressure in time from the production of the fluid connection.

The fluid medium can be received in the receptacle in a manner free from bubbles.

A pressure level in the fluid medium and a storage period can be determined in such a manner that there can be no gas bubbles in the receptacle.

A pressure level in the fluid medium can be sufficient in order completely to dissolve an initially present gas bubble in the fluid medium over time such as over a period of time of at most one month in one embodiment and of at most one week in another embodiment.

The transport and transfer receptacle can be configured in such a manner that, during transport and storage of the transport and transfer receptacle, the fluid medium can come into contact exclusively with a container wall of the container and a closure element of the container such as, for example, a stopper.

The methods and devices proposed can have numerous advantages over known methods and devices. Numerous injection and transfer systems for sterile liquids are used worldwide. As a rule, the liquid, after being decanted, can be stored in an unpressurized manner, i.e. under atmospheric pressure. Only upon or during use is the pressure in the liquid increased in order to carry out a transfer. From the outset, syringes simply on account of the structure have a fluid connection for the subsequent transfer. Furthermore, there are what can be referred to as carpules which have a septum via which a fluid connection can be produced. In addition, there are what are referred to as injection pens in which first of all a fluid connection is produced and then the pressure is increased. Furthermore, special forms of syringes and carpules, in which the fluid connection is not produced until directly upon use and together with the increased pressure, can be also conceivable. However, systems of this type have in general different disadvantages which can be overcome in a simple and reliable manner by the above-described preferred features. While, for example, syringes containing a fluid connection generally have at least three components, namely the cylindrical body, the displaceable stopper and the covering of the fluid connection, which components interact with the product, the transport and transfer receptacle can be configured in such a manner that the container can initially be produced without a fluid connection. The simplest possible form of the container can be a tube which can be closed on one side and, after being filled, can be closed by a displaceable stopper. Other embodiments can be, for example, carpules and tubes having two displaceable stoppers. In addition to containers with a rigid container wall, for example made of glass and/or plastic, containers which can have a moldable or flexible wall and which may not necessarily have to be completely composed of a dimensionally rigid and/or elastic material can be conceivable.

The proposed transport and transfer receptacle, in which the fluid medium can be charged with positive pressure, can have advantages in the case of highly viscous, fluid media.

Highly viscous medicaments which can no longer be injected by conventional syringes can thereby be metered and/or injected.

A further advantage can comprise in the fact that, in conventional systems, air bubbles arising during the decanting operation generally may no longer removable later and/or may only be removed manually by the user. In contrast thereto, the fluid medium in the container can be placed under positive pressure via the energy unit, which can comprise one or more different types of energy carrier. The pressure level selected can lie above the required or desired transfer pressure for transferring the fluid medium out of the interior of the container. For example, in order to increase the pressure, the energy unit can have one or more spring elements which can be realized in a technically simple manner. The at least one spring element can comprise, for example, at least one purely mechanical spring or else one or more gas-filled springs and/or one or more liquid-/gas-filled springs. A positive secondary effect can arise with the increase in pressure, at which bubbles present in the container because of the increased gas solubility can disappear. Ideally, the pressure can already be increased at the manufacturer and can remain until use at the level required for injection and/or for transfer of the liquid out of the container. The transport and transfer receptacle therefore can have an integrated, system-induced tightness check. The integrity of the transport and transfer receptacle can be checked in a simple manner both during production and by the user. A tightness check can also be carried out by the user, for example before use, since, for example, a leakage can involve the container emptying over a prolonged storage time.

A transfer of the fluid medium out of the interior of the container can be realized in a simple manner such as, for example, exclusively by production of the fluid connection such as, for example, by perforation of the perforable section of the container.

The container with the energy unit can also be produced and sold as an independent assembly without the injection part. In this case, the optional transfer system and/or the optional injection system may not assembled from a plurality of assemblies, for example of the transport and transfer receptacle and a further injector assembly, until at the user.

The transport and transfer receptacle can therefore be part of an injector or can be designed as an injector. For example, an autoinjector may be involved. Autoinjectors can have a growing importance, since there is generally a trend to self-medicate in practice. Autoinjectors can be used, for example, for smaller volumes of up to about 1 ml. Accordingly, the container can be configured, for example, in order to receive a quantity of about 0.1-1.0 ml of fluid medium. However, other liquid quantities can be in principle also possible, for example liquid quantities of about 0.5 ml-200 ml such as, for example of about 1 ml-100 ml. Greater liquid quantities can be realized by the fact that, the perforating of the at least one perforable section of the container can be reversible, and therefore, for example, a transfer of the fluid medium out of the container can be interrupted and optionally can be subsequently resumed. There can therefore be a high degree of flexibility with regard to the configuration of the transfer process, for example with regard to transferred quantities of fluid, transfer durations, discontinuation of the transfer and other options.

In known autoinjectors, the needle of the injector can generally be inserted into the body tissue and the liquid can be displaced by the build-up of pressure in the syringe or carpule. In addition to autoinjectors, there can also be reusable injection systems, such as, for example, insulin pumps which can inject relatively large quantities of liquid, sometimes little by little, over a long period. In the case of systems of this type too, the pressure required for the transfer can customarily be built up only at the moment of the transfer. However, known systems of this type, such as autoinjectors or medication pumps are generally unfavorable for injecting relatively large quantities of liquid, since, for example, the autoinjector has to remain at the injection site for the entire injection period. In addition, the user can be generally, depending on mobility, greatly limited in the choice of injection sites. In many cases, an optical check of the progress and end of the injection can be impeded.

By contrast, by the transport and transfer receptacle, the basic principle of known autoinjectors can be divided into two functional groups, namely, firstly, the functional group which can have the container, the energy unit and the triggering mechanism, wherein the latter can comprise, for example, the at least one perforating element, and a second group which can be responsible for injection into the tissue. The latter group can comprise, for example, at least one infusion kit. The two functional groups can be connected rigidly or flexibly to each other, in the latter case, for example, via at least one tubing connection.

A plurality of advantages can arise for the user. An injection into the body tissue can thus take place, for example, independently of the actual insertion and/or independently of transfer of the fluid medium out of the container. The actual injection into the body tissue can also take place at sites which can be difficult to see into and are not easily checkable wherein the transport and transfer receptacle can optionally be arranged in a region visible for the user. For example, the transport and transfer receptacle can be of completely or partially transparent design, for example by the container and also the external container being of transparent design in such a manner that the user can check, for example, a filling level of the container.

The transport and transfer receptacle and optionally the injector can be moved during the injection, which may be more pleasant for long injection times. Furthermore, the injector can be completely or partially readily seen and the course of the injection can be better checked. The transport and transfer receptacle can optionally contain a start/stop function, for example by a corresponding switching element. The injection can take place in one or else in more stages. Furthermore, the transport and transfer receptacle can be designed in such a manner that it can completely dispense with electric drives.

Referring initially to FIG. 1, FIG. 1 illustrates a first embodiment of a transport and transfer receptacle 110 for a fluid medium 112 such as, for example, a sterile liquid. In the embodiment illustrated, the transport and transfer receptacle 110 can comprise a container 114, which, in the embodiment illustrated, can be designed as a tubular container closed on one side and, according to FIG. 1, can be open downward. The container 114 can receive the fluid medium 112. The container 114 can have a container wall 115 which can be produced, for example, entirely or partially from glass and/or plastic. For example, the container wall can be of entirely or partially transparent design, and therefore the fluid medium 112 can be seen from the outside. The container wall 115 can be, for example of substantially tubular design, for example in the form of a cylindrical tube which can be closed on one side. The container 114 can be closed by a closure element in the form of a moveable, perforable stopper 116 which can form a perforable section 118 of the container 114. The stopper 116 can constitute one possible embodiment of a closure element which can close the container 114. In the region of the perforable section 118, the stopper 116 can have, for example, a recess 122 pointing toward an interior 120 of the container 114 and/or a recess 124 pointing away from the interior 120, and therefore the stopper 116 can be weakened in the region of the perforable section 118 and an at least substantially complete emptying of the interior 120 during a use of the transport and transfer receptacle 110 can be facilitated, for example, by the recess 122.

In the embodiment illustrated in FIG. 1, the container 114 can be accommodated in a closed state in an external container 126. The external container 126 can likewise of at least partially transparent design, and therefore, for example, a filling level of the container 114 can be observed through the external container 126. In the embodiment illustrated, the external container 126 optionally can have two container parts 128, 130 which, in the embodiment illustrated, are illustrated in the form of one container part 128 which can be designed as a hollow cylinder, and in the form of one container part 130 which can be designed as a cap part. However, other configurations can also be possible. The container parts 128, 130 can be connectable to each other via one or more connecting elements 132 of the container part 128 and/or of the container part 130 such that the external container 126 can, for example, be closeable.

Furthermore, the transport and transfer receptacle 110 can comprise an energy unit 134 which can comprise an energy accumulator such as, for example, a mechanical and/or hydraulic energy accumulator such as, for example, in the form of one or more spring elements 136. For example, the energy unit 134 can be entirely or partially arranged in an intermediate space 138 between the external container 126 and the container 114. The spring element can be supported, for example, as shown in FIG. 1, at one end thereof on the external container 126 and at an opposite end against the container 114, for example at a peripheral edge 140 of the container 114 as likewise illustrated in FIG. 1.

As shown in FIG. 1, the energy unit 134 can optionally be designed in such a manner that the container 114 can be pressed by the stopper 116 against an abutment 142. In the embodiment illustrated, the abutment 142 can be designed by way of example as part of the external container 126 such as, for example, as part of the container part 130. The abutment 142 may be designed, for example, in the form of a punch 144 which can project into an interior 120 of the container 114 and can act on the stopper 116. Pressure can be exerted in this manner or in a different manner by the energy unit 134 on the fluid medium 112 located in the container 114, which pressure can be maintained during a storage period of the transport and transfer receptacle 110. The stopper 116 and/or the abutment 142, in interaction with the spring element 136, can therefore likewise be understood as being parts of the energy unit 134.

During the production of the transport and transfer receptacle 110, first of all, for example, the container 114 can be filled and closed, after which the container 114 can be accommodated in the external container 126. By connection of the container parts 128, 130, the energy unit 134 and the spring element 136, which can act as an energy accumulator, can be tensioned and the external container 126 can be closed.

As shown in FIG. 1, the abutment 142 can be designed in such a manner that the perforable section 118 can be perforated by the abutment 142. For this purpose, the abutment can comprise, for example, at least one perforation opening 146 which, in the embodiment illustrated in FIG. 1, can be in the form of an elongated perforation channel which can extend through the abutment 142 and which can be formed, for example, substantially parallel to a longitudinal axis of the tubular container 114. On an outer side of the external container 126 which can point toward an exterior 148, the perforation opening 146 can optionally be closed by at least one closure element 150, for example at least one further stopper. The closure element 150 can be designed in such a manner that the closure element can be opened manually by a user, for example by a tab.

For the use of the transport and transfer receptacle 110, first of all the closure element 150 can optionally be removed. Subsequently, the stopper 116 and the perforable section 118 thereof can be perforated with a perforating element, which is not illustrated in FIG. 1, for example a cannula, through the perforation opening 146, with a fluid connection to the interior 120 being produced. This production of the fluid connection can take place completely independently of pressurization of the fluid medium. The transfer of the fluid medium 112 out of the interior 120 into the exterior 148 or into a fluid device (not illustrated) can then take place through the perforating element, for example a cannula. The perforating can optionally be stopped again after partial emptying of the container 114, with the fluid connection being closed again.

Furthermore, distances a and b are indicated symbolically in FIG. 1. For complete emptying of the container 114, the distance b can be greater than or at least equal to the distance a. The shape of the container wall 115 can be designed in such a manner that, even when the stopper 116 is inserted into the interior 120 to the maximum, no dead volumes which cannot be emptied can be produced, and this can be realized, for example, by a flat base of the container 114.

Furthermore, the transport and transfer receptacle 110 can be designed in such a manner that parts thereof, at least the container 114 and optionally one or more further parts, can be entirely or partially accommodated in a packaging 151. The packaging 151 is merely indicated symbolically in FIG. 1 and can comprise, for example, a plastics packaging such as, for example, a film packaging. The packaging 151 can be conceptually part of the transport and transfer receptacle 110, even if the packaging can be opened and/or entirely or partially removed, for example before a use. The remaining parts of the transport and transfer receptacle 110, with the exception of the packaging 151 can form, for example, one or more use units which can be used for transferring the fluid medium 112 out of the interior 120. At least the container 114 and optionally the energy unit 134 can be accommodated in the packaging 151, for example, in a state in which the fluid medium 112 can be charged with positive pressure by the energy unit 134.

Figure 2:
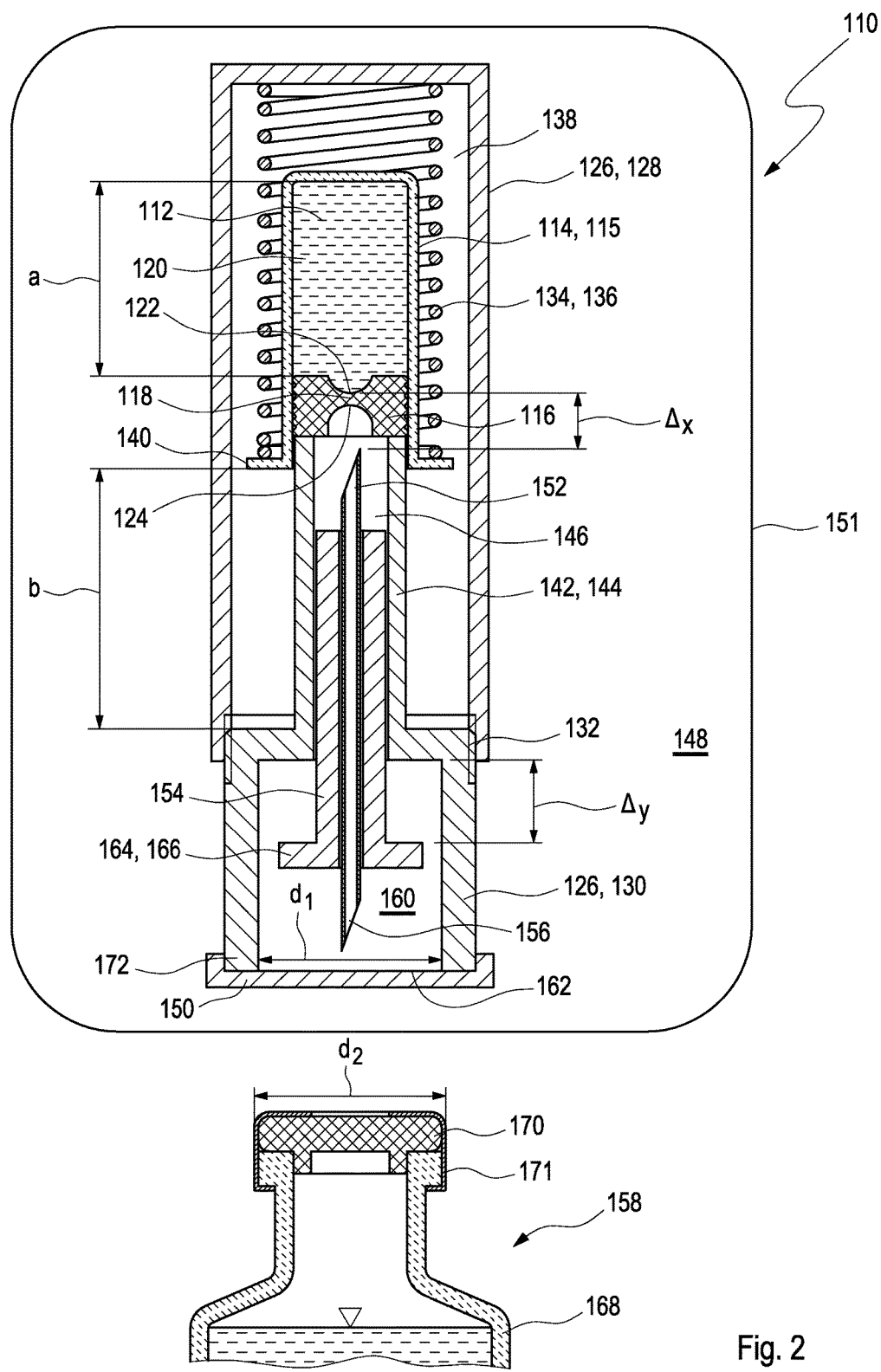
FIG. 2 illustrates a transport and transfer receptacle with a coupling for coupling to a vessel according to an embodiment of the present disclosure.

FIG. 2 illustrates an alternative embodiment of FIG. 1 of a transport and transfer receptacle 110, again, analogously to FIG. 1, in a sectional illustration. The transport and transfer receptacle 110 can first of all again be designed analogously to FIG. 1 and can have, for example, a container 114 which can receive the fluid medium 112 and can have a stopper 116. The stopper 116 can again be designed analogously to FIG. 1 and can, for example, again have recesses 122, 124 in the region of a perforable section 118. Furthermore, an external container 126 which again can optionally have a plurality of container parts, here two container parts 128, 130, can again also be provided. The container parts 128, 130 can again be connected to each other, for example, via one or more connecting elements 132, for example again via one or more screw connections.

An energy unit 134 can again be provided in an intermediate space 138 between the external container 126 and the container 114, which energy unit can again comprise, for example, an energy accumulator in the form of, for example, a spring element 136. Also in this regard, reference can again be made to the above description of FIG. 1. The spring element 136 can again be supported, for example, on an edge 140 of the container 114.

In the embodiment illustrated, the external container 126 can again comprise an abutment 142 which can be, for example, part of the container part 130 and which can act on the stopper 116. In this regard, reference can be made to the above description of FIG. 1. The abutment 142 can again be designed, for example, as a punch 144 and again can comprise a perforation opening 146.

Furthermore, in the embodiment illustrated, a perforating element 152, for example in the form of a cannula pointing toward the stopper 116, can be provided in the external container 126, completely or partially within the perforation opening 146. The perforating element 152 can be mounted, for example, moveably within the external container 126 in such a manner that the perforating element can carry out a perforating movement, directed upward in FIG. 2, for perforating the perforable section 118. The perforating element 152 can be accommodated, for example, in a guide element 154 which, for its part, can be mounted moveably in the perforation opening 146. Alternatively or in addition, the perforating element 152 can also be mounted directly in the perforation opening 146. Various configurations can be possible.

In the embodiment illustrated, the transport and transfer receptacle furthermore optionally can have an injection element 156. The injection element 156, which can again comprise, for example, a cannula, can be configured for transferring the fluid medium 112 into a vessel 158 formed separately from the transport and transfer receptacle and/or for injection of the fluid medium 112 into a body tissue. The vessel 158 can be, for example, a receptacle in which optionally, for example, a freeze-tried powder can be accommodated, which powder can be intended to be dissolved, for example by a solvent supplied by the transport and transfer receptacle 110, before further use. The injection element 156 can be fluidically connected to the perforating element 152, thus permitting transfer of the fluid medium 112 through the perforating element 152 and through the injection element 156.

The perforating element 152 and the injection element 156 can be connected, for example as shown in FIG. 2, rigidly to each other or else via a flexible connection, for example a tubing connection. The rigid connection can be realized, for example, by the perforating element 152 and the injection element 156 forming mutually opposite ends of an injection cannula which can be connected on both sides to a point, a cutting edge or a similar means.

In the embodiment illustrated in FIG. 2, the injection element 156 can project by way of example into a cavity 160 of the external container 126, which cavity, as shown in FIG. 2, can be designed separately from the intermediate space 138 or which can also be formed entirely or partially identically thereto. The cavity 160 can be closeable, for example by a closure element 150, for example a cap, in order to protect the injection element 156. The guide element 154, which can be connected rigidly to the perforating element 152 and/or to the injection element 156, can have, for example, at the end thereof pointing toward an opening 162 of the cavity 160, a widened portion 164 which can make it possible for the guide element 154 to be operable.

The guide element 154 can optionally also be operable from the outside, and therefore a perforating movement can be guided manually, for example. In this case, the widened portion 164 can be accessible from the outside, for example through a recess in the container 130, and/or can project outward, into an exterior 148, and therefore the widened portion 164 can also serve as a switching element 166 in order to control the perforating of the perforable section 118. The widened portion 164 can be intended to be at such a distance from a beginning of the perforation opening 146 and/or from a stop for the widened portion 164 (spacing Δy in FIG. 2) that the widened portion 164 can move upward by at least an amount which corresponds to a spacing between the point of the perforating element 152 and the interior 120 of the container 114 (spacing Δx in FIG. 2). It can thereby be ensured that, for the purpose of a perforating movement, the perforating element 152 can move upward at least to an extent such that the stopper 116 can be completely perforated and a fluid connection between the interior 120 and the exterior 148 can be produced through the stopper 116. Furthermore, the distances a and b are shown again in FIG. 2, analogously to FIG. 1. For maximum emptying, the distance b can again be greater than or at least equal to the distance a.

The vessel 158 which can be formed separately from the transport and transfer receptacle 110 can be, for example, as shown in FIG. 2, a vial 168 and/or another vessel, in particular glass vessel, which can be closed, for example, at the upper end thereof by a septum 170. The septum 170 can be fixed, for example, by a flanged cap 171, likewise indicated in FIG. 2, or by a different type of holding element. However, in principle, other configurations of the vessel 158 can also be possible. The transport and transfer receptacle 110 can comprise, for example, one or more couplings 172 which can permit mechanical coupling to the vessel 158. In the embodiment illustrated, the coupling 172 can comprise, for example, a collar which can be matched, for example, in terms of the inside diameter thereof to an outside diameter of the septum 170 and/or of a neck of the vial 168. This is indicated in FIG. 2 by the diameter $d_1$ and $d_2$ wherein the following should apply: $d_1 \geq d_2$ or $d_1 \geq d_2$.

The fluid medium 112 can be transferred out of the interior 120 of the container 114 into the vessel 158, for example, in such a manner that first of all the closure element 150 can optionally be removed. Subsequently, the vessel 158 can be coupled up by the upper side of the septum 170 being pressed onto the widened portion 164 of the guide element 154. In the process, the injection element 156 can perforate the septum 170, and at the same time the guide element 164 can be pushed upward in FIG. 2. By this means, the perforating element 152 can perforate the perforable section 118 of the stopper 116 at the same time or with a time delay, and the fluid connection to the interior 120 can be produced. By the positive pressure with which the fluid medium 112 can be charged, the fluid medium 112 can be transferred through the perforating element 152 and the injection element 156 and through the septum 170 into the vessel 158. One or more liquids can already be located in the vessel 158. Overall, a sterile transfer of the fluid medium 112 can thereby be possible.

Figure 3:
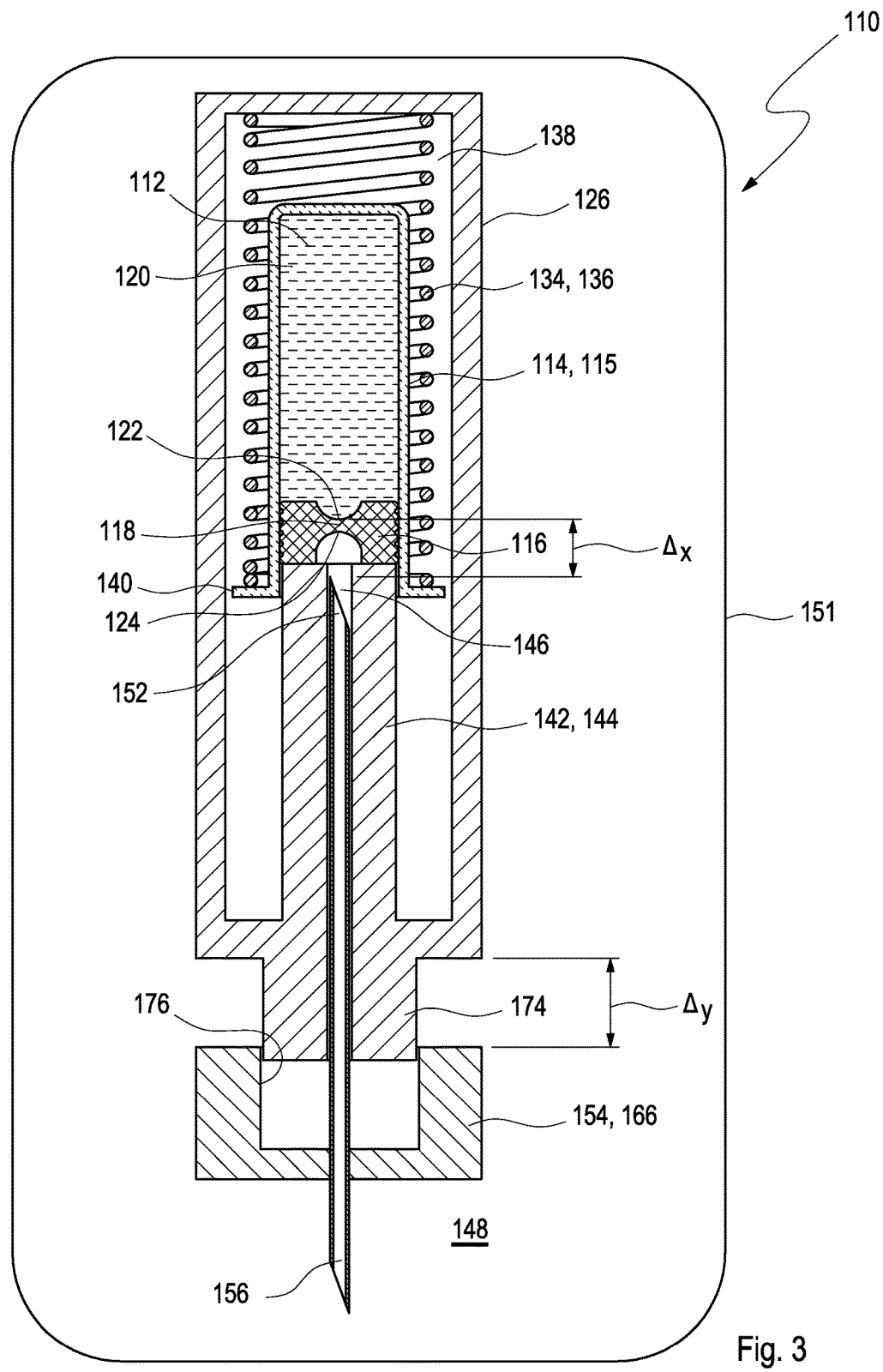
FIG. 3 illustrates a transport and transfer receptacle with an injection element according to an embodiment of the present disclosure.

FIG. 3 shows a further embodiment of a transport and transfer receptacle 110 in an illustration analogous to FIGS. 1 and 2. The transport and transfer receptacle 110 can first of all be designed analogously to the exemplary embodiment according to FIG. 2, and therefore reference can be substantially made to the above description of FIG. 2. An abutment 142, against which the stopper 116 can be pressed by the energy unit 134, can again be provided, analogously to the example in FIGS. 1 and 2. In contrast to the embodiments in FIGS. 1 and 2, the external container 126 is illustrated here as a single part, but in principle can again also be of multi-part design, for example by one or more connecting elements 132 analogously to FIGS. 1 and 2, and therefore, for example, a contact pressure of the abutment 142 against the stopper 116 can also be set.

Furthermore, in contrast to the embodiment according to FIG. 2, although a perforating element 152 can again also be partially accommodated in a perforation opening 146 of the abutment 142, the perforating element, in the embodiment illustrated according to FIG. 3, may not be accommodated in a guide element 154, but rather can be mounted directly in the perforation opening 146. However, in principle, a configuration with an additional guide element 154, analogously, for example, to the configuration according to FIG. 2, can also be possible.

The perforating element 152 can again be configured, for example, as a continuous cannula, at the end of which opposite the perforating element 152, for example, an injection element 15b can again be accommodated. The injection element 156 can, for example, project out of the transport and transfer receptacle 110, in the embodiment illustrated. The perforating element 152 and the injection element 156 can be connected, for example, fluidically to each other again, for example by the cannula.

Although, in the embodiment according to FIG. 3, a guide element 154 arranged in the perforation opening 146 may not be provided, a guide element 154 which can be arranged outside the perforation opening 146 can be provided. The guide element 154 can also again serve, for example, as a switching element 166, for example in order to effect a perforating of the stopper 116 manually or again, for example, by pressing against a septum 170. For this purpose, the switching element 166 can be pushed upward, for example, in FIG. 3, wherein, for example, an extension 174 on the external container 126 can engage in a recess 176 in the switching element 166 such that the movement of the switching element 166 can be guided. Therefore, analogously to the illustration according to FIG. 2, FIG. 3 illustrates a second switch position of the switching element 166, in which the stopper 116 may not be perforated and therefore a fluid connection to the interior 120 may not be produced. If, by contrast, the switching element 166 in FIG. 3 can be moved upward, as also in FIG. 2, the perforating element 152 can penetrate the stopper 116 and the fluid connection can be produced. The switching element 166 can then be in a first switch position, wherein the fluid connection can exist in the first switch position. This production of the fluid connection can be reversible, and therefore the switching element 166 can also be transferred again from the first switching position into the second switching position, for example by the switching element 166 being pulled downward again in FIGS. 2 and 3. The switching element 166 can be actuated manually or else automatically, for example when the transport and transfer receptacle 110 can be placed onto at least one vessel 158 and/or during an injection operation. A mixed form of the embodiments illustrated in FIGS. 2 and 3 can also be possible, for example, by the guide element 154 in the embodiment according to FIG. 3 having an extension which can engage in the perforation opening 146 and can be guided there.

Figure 4:
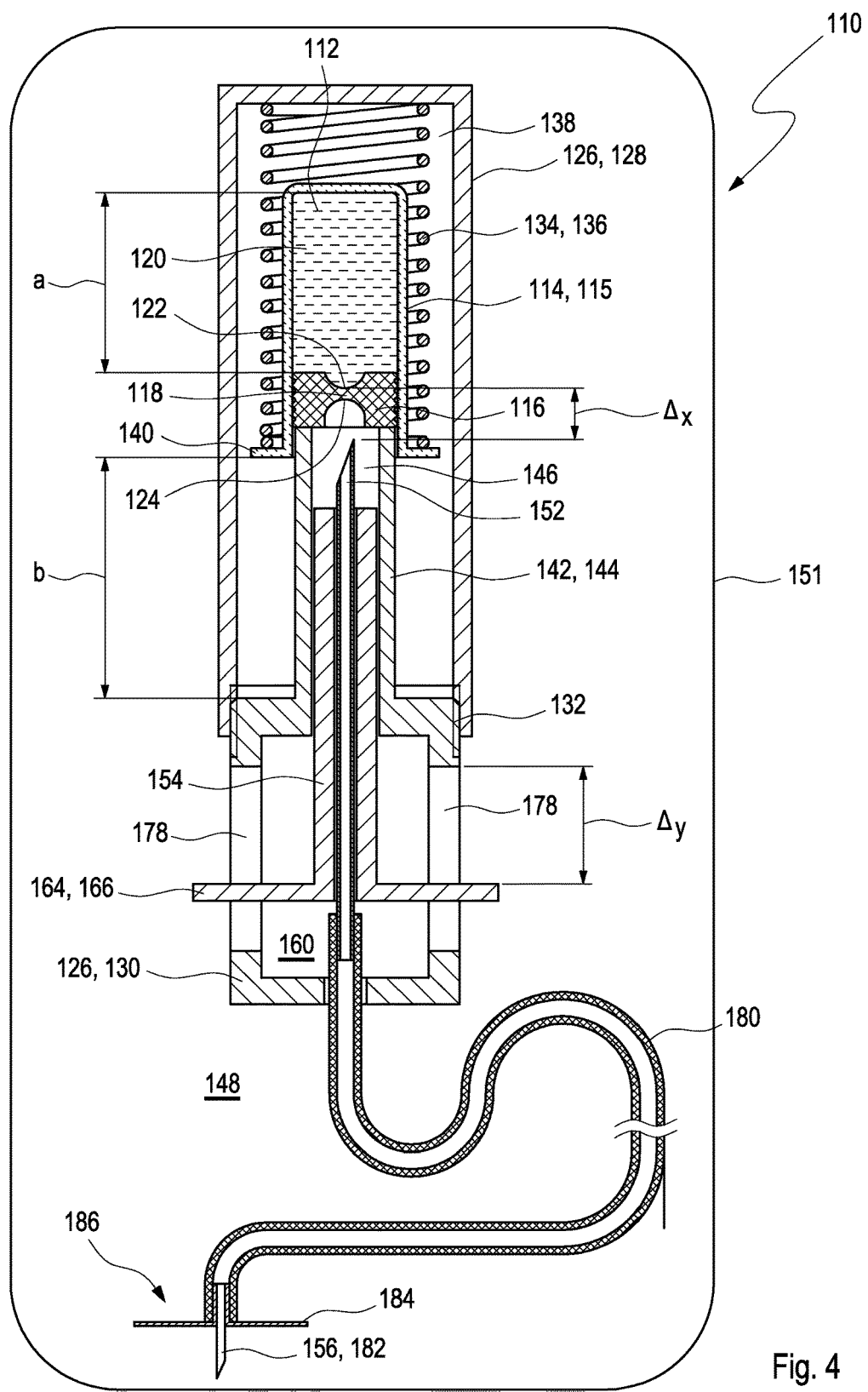
FIG. 4 illustrates a transport and transfer receptacle with a switching element and with optional coupling to a tubing connection according to an embodiment of the present disclosure.

FIG. 4 shows a further modification of the embodiment of the transport and transfer receptacle 110 according to FIG. 2. This configuration first of all can substantially correspond again to the configuration according to FIG. 2, and therefore reference can be substantially made to the above description. In contrast to the embodiment according to FIG. 2, in the embodiment illustrated according to FIG. 4, the switching element 166 can be guided out of the cavity 160 of the container part 130 such that the switching element can be easily operable from the exterior 148. The switching element 166 can thereby be transferred, for example, from the switch position illustrated in FIG. 4 into a switch position in which the perforating element 152 can perforate the perforable section 118 of the stopper 116, by the switching element 166 in FIG. 1 being guided upward. In order to guide the switching element 166 out of the cavity 160, one or more openings 178 can be provided in the wall of the cavity 160.

A further difference to the embodiment according to FIG. 2, can comprise in the fact that the perforating element 152 may not be connected rigidly to an injection element 156. Instead, an injection element 156 which can be connected fluidically to the perforating element 152 via a flexible connection 180, in particular via a flexible, sterile tubing connection can be provided. One end of the flexible connection 180 can be coupled, for example in the cavity 160 or even in the exterior 148, to a cannula end opposite the perforating element 152. At an opposite end, the flexible connection 180 can be connected to the injection element 156. The injection element 156 can be designed, for example, as illustrated in the embodiment according to FIG. 4, as an infusion cannula 182 which, together with a plaster 184 for application to a patient's skin, can be part of an infusion kit 186. However, in principle, other configurations can also be possible.

By the arrangement illustrated in FIG. 4, an infusion operation can be carried out in a simple and reliable manner. For example, insertion of the injection element 156 into a body tissue of a user can be completely decoupled mechanically from production of the fluid connection through the stopper 116. For example, the injection element 156 can first of all be inserted and the plaster 184 adhesively bonded onto the skin surface of the user. Subsequently, for example by actuation of the switching element 166, the fluid connection can be produced, and therefore the infusion can start. The infusion can also be reversibly interrupted again, likewise again by actuation of the switching element 166. Alternatively, even before the injection element 156 is inserted into the skin surface, the flexible connection 180 can already be completely or partially filled with the fluid medium 112, for example by the switching element 166 being actuated a first time. The fluid connection to the interior 120 can subsequently be interrupted again by actuation of the switching element 166, the injection element 156 can be inserted into the body tissue, and the switching element 166 can subsequently be actuated again in order to start the actual infusion. A bubble-free injection can thereby be carried out.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A transport and transfer receptacle for storing and supplying at least one fluid medium, wherein the transport and transfer receptacle comprises:
   at least one container with the fluid medium accommodated therein, wherein the container has a container wall and at least one perforable section, wherein the perforable section is displaceable relative to the container wall and wherein, by perforating the perforable section, a fluid connection to an interior of the container can be produced for the purpose of removing the fluid medium from the container;
   at least one integrated energy unit, wherein the energy unit effects emptying of the fluid medium from the container when the transport and transfer receptacle is used, wherein the energy unit charges the fluid medium in the container with positive pressure, wherein the positive pressure can be maintained until the fluid medium is removed, and wherein the energy unit acts directly upon and mechanically on the perforable section; and
   at least one packaging, wherein at least the container in the state charged with positive pressure is received in the packaging.

2. The transport and transfer receptacle according to claim 1, further comprising,
   at least one external container, wherein the container is at least partially accommodated in the external container, wherein the external container and the energy unit are configured in such a manner that the fluid medium is pressurized during one or both of connection of the external container to the container or during closing of the external container.

3. The transport and transfer receptacle according to claim 2, wherein the energy unit is mechanically tensioned.

4. The transport and transfer receptacle according to claim 1, wherein the energy unit comprises at least one spring element, wherein the spring element presses at least part of the container against at least one abutment of the transport and transfer receptacle.

5. The transport and transfer receptacle according to claim 4, wherein the spring element is a helical compression spring.

6. The transport and transfer receptacle according to claim 4, wherein the spring element presses the perforable section against the at least one abutment of the transport and transfer receptacle.

7. The transport and transfer receptacle according to claim 4, wherein the spring element presses a perforable stopper against the at least one abutment of the transport and transfer receptacle.

8. The transport and transfer receptacle according to claim 1, wherein the transport and transfer receptacle comprises at least one perforating element for perforating the perforable section.

9. The transport and transfer receptacle according to claim 1, further comprising,
   at least one injection element, wherein the injection element is configured to be inserted into at least one of a human or animal body tissue or into a vessel formed separately from the container.

10. The transport and transfer receptacle according to claim 9, wherein the transport and transfer receptacle is designed in such a manner that producing a fluid connection between the injection element and the interior and inserting the injection element into the human or animal body tissue and/or into the vessel formed separately from the container form separate working steps.

11. The transport and transfer receptacle according to claim 9, wherein the transport and transfer receptacle has at least one switching element, wherein the switching element, in at least one first switch position, maintains the fluid connection to the interior of the container by perforating the perforable section, wherein the switching element, in at least one second switch position, interrupts the fluid connection.

12. The transport and transfer receptacle according to claim 11, wherein the switching element, in the at least one second switch position, interrupts the fluid connection by interrupting the perforating of the perforable section.

13. The transport and transfer receptacle according to claim 1, wherein the transport and transfer receptacle is for storing and supplying at least one sterile liquid.

14. The transport and transfer receptacle according to claim 1, wherein the perforable section is a displaceable stopper.

15. The transport and transfer receptacle according to claim 1, wherein the energy unit effects the complete emptying of the fluid medium from the container.

* * * * *